(12) United States Patent
Lee et al.

(10) Patent No.: US 9,309,515 B2
(45) Date of Patent: *Apr. 12, 2016

(54) APTAMER WHICH SELECTIVELY BINDS TO ERBB2 RECEPTOR AND USES THEREOF

(75) Inventors: Jung Hwan Lee, Pohang-si (KR); Young Chan Chae, Pohang-si (KR); Youngdong Kim, Pohang-si (KR); Hyungu Kang, Daegu (KR); Jong Hun Im, Seoul (KR); Jong In Kim, Pohang-si (KR); Ki Seok Kim, Pohang-si (KR); Sung Key Jang, Pohang-si (KR); Il Ung Oh, Cheongju-si (KR); Min Jeong Choi, Seoul (KR); Won Jun Kang, Goyang-si (KR)

(73) Assignees: POSTECH ACADEMY-INDUSTRY FOUNDATION, Pohang (KR); KOREA FOOD & DRUG ADMINISTRATION, Cheongwon-Gun (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/128,152

(22) PCT Filed: Aug. 10, 2011

(86) PCT No.: PCT/KR2011/005852
§ 371 (c)(1),
(2), (4) Date: Apr. 3, 2014

(87) PCT Pub. No.: WO2012/176952
PCT Pub. Date: Dec. 27, 2012

(65) Prior Publication Data
US 2015/0005368 A1    Jan. 1, 2015

(30) Foreign Application Priority Data
Jun. 24, 2011    (KR) .................. 10-2011-0061939

(51) Int. Cl.
*C12N 15/11*    (2006.01)
*C12N 15/115*    (2010.01)
*A61K 31/7088*    (2006.01)
*G01N 33/574*    (2006.01)
*A61K 47/48*    (2006.01)

(52) U.S. Cl.
CPC .......... *C12N 15/115* (2013.01); *A61K 31/7088* (2013.01); *A61K 47/48215* (2013.01); *G01N 33/5748* (2013.01); *C12N 2310/16* (2013.01); *C12N 2310/335* (2013.01); *C12N 2310/3535* (2013.01); *C12N 2320/30* (2013.01); *G01N 2333/71* (2013.01); *G01N 2333/91205* (2013.01)

(58) Field of Classification Search
CPC ............. C12N 15/115; A61K 31/7088; A61K 47/48215
See application file for complete search history.

(56) References Cited

U.S. PATENT DOCUMENTS 8,785,132 B2 *    7/2014    Chae ........................... 435/6.12
2009/0004667 A1    1/2009    Zichi

OTHER PUBLICATIONS

Vaught et al. J. Am. Soc. 2010, 132: 4141-4151.*
Kim, M.Y. and Jeong, S., "In vitro selection of RNA aptamer and specific targeting of ErbB2 in breast cancer cells," Oligonucleotides. vol. 21, No. 6, p. 1-6 (Jun. 6, 2011).
Kang, H.S. et al., "Isolation of RNA Aptamers targeting HER-2 overexpressing breast cancer cells using cell-SELEX," Bulletin of the Korean Chemical Society. vol. 30(8), pp. 1827-1831 (Aug. 20, 2009).
Kunz, C. et al., "Peptide aptamers with binding specificity for the intracellular domain of the ErbB2 receptor interfere with AKT signaling and sensitize breast cancer cells to Taxol," Molecular Cancer Research. vol. 4(12), pp. 983-998 (Dec. 2006).
Kuwahara, M. and Sugimoto, N., "Molecular evolution of functional nucleic acids with chemical modifications," Molecules. vol. 15(8), pp. 5423-5444 (Aug. 9, 2010).
Lee, Jung Hwan, "Research of effect and stability for aptamer formation—in vivo selection and in vivo evolution" POSTECH Academy-Industry Foundation (Nov. 30, 2010).

* cited by examiner

Primary Examiner — Brian Whiteman
(74) Attorney, Agent, or Firm — Lex IP Meister, PLLC

(57) ABSTRACT

Disclosed are a DNA aptamer specifically binding to the Her2 (ERBB2) receptor involved in the onset of breast cancer, a composition for the suppression of cancer metastasis comprising the same as an active ingredient, and a composition for the diagnosis of cancer comprising the same as an active ingredient. Due to its binding mechanism being different from that of the conventional antibody, the aptamer can be effectively used for suppressing cancer metastasis and diagnosing cancer.

14 Claims, 14 Drawing Sheets

Day 0       Day 6

APTAMER WHICH SELECTIVELY BINDS TO ERBB2 RECEPTOR AND USES THEREOF

BACKGROUND

1) Field of the Invention

Provided is a DNA aptamer selectively binding to the breast cancer-related Her2 (ERBB2) receptor, and a composition for suppressing cancer metastasis or for diagnosing cancer, comprising the same as an active ingredient.

2) Background of the Invention

Breast cancer is the most common cancer in women in advanced countries, such as in the United States and Europe, arising as the primary cause of death among women 40 to 55 years old in the United States. One in 9 women will develop breast cancer at some point during her lifetime. Each year the number of new breast cancer cases increases by 15%. In South Korea, breast cancer accounted for approximately 11.9% of female cancer cases in 1995, and is the third most common cancer in terms of incidence after uterine cervical cancer and stomach cancer. The mortality of breast cancer was reported to come after stomach cancer, hepatic cancer, uterine cancer, and lung cancer in women, and is increasing each year.

Of the total breast cancer cases, approximately 20-25% were observed to have the overexpression of HER-2 protein (ERBB2). It is known that breast cancer with HER-2 overexpression proceeds faster, is more aggressive and responds at a lower yield to Tamoxifen or other particular chemotherapy regimens than that without HER-2 overexpression. Herceptin (Trastuzumab, Genentech), a humanized monoclonal antibody binding to the HER-2 receptor, disrupts the dimerization of the Her-2 receptor to interfere with the signaling of the Her-2 receptor, whereby selective attack against breast cancer cells can be achieved, resulting in a significant increase in the survival of breast cancer patients. Now, herceptin, which selectively targets the Her-2 receptor, has becomes a leading anticancer drug thanks to its sharp increase in sales each year since its launch.

However, herceptin, when administered alone, elicits a response yield as low as approximately 20%, and imparts a very large economic burden to the patient for one year. In addition, this antibody may cause cardiac toxicity in some patients, and herceptin resistance occurs in some patients who have been administered the drug for one year and thus do not respond to herceptin regimens. This is attributed to the fact that herceptin does not act on the exact site for interfering with the dimerization of the Her-2, but on a false site thus resulting in a reduced binding force. Accordingly, many pharmaceutical companies have pursued research and development of alternatives to herceptin, such as Pertuzumab.

In this invention, focus is made on the development of an aptamer which selectively binds to the Her-2 receptor and which overcomes the disadvantages of herceptin, with the expectation that it can be used for the treatment and diagnosis of breast cancer and can effectively remove breast cancer cells when administered in combination with herceptin, thanks to its binding mechanism being different from that of the conventional antibody.

SUMMARY OF THE INVENTION

An embodiment provides an ERBB2 aptamer which specifically binds to ERBB2 and has modified dUTP (deoxyuracil) with a hydrophobic group, such as a naphthyl group, a benzyl group, a pyrrolebenzyl group, tryptophan, introduced at the 5' position thereof.

Another embodiment provides a composition for the treatment of cancer, comprising the ERBB2 aptamer as an active ingredient.

A further embodiment provides a method for treating cancer, comprising administering the ERBB2 aptamer to a subject in need thereof.

A still further embodiment provides the use of the ERBB2 aptamer in the treatment of cancer.

Still another embodiment provides a composition for the diagnosis of cancer, comprising the ERBB2 aptamer as an active ingredient.

A yet further embodiment provides a method for diagnosing cancer, using the ERBB2 aptamer.

Yet another embodiment provides the use of the ERBB2 aptamer in the diagnosis of cancer.

DETAILED DESCRIPTION OF THE INVENTION

Figure 1:
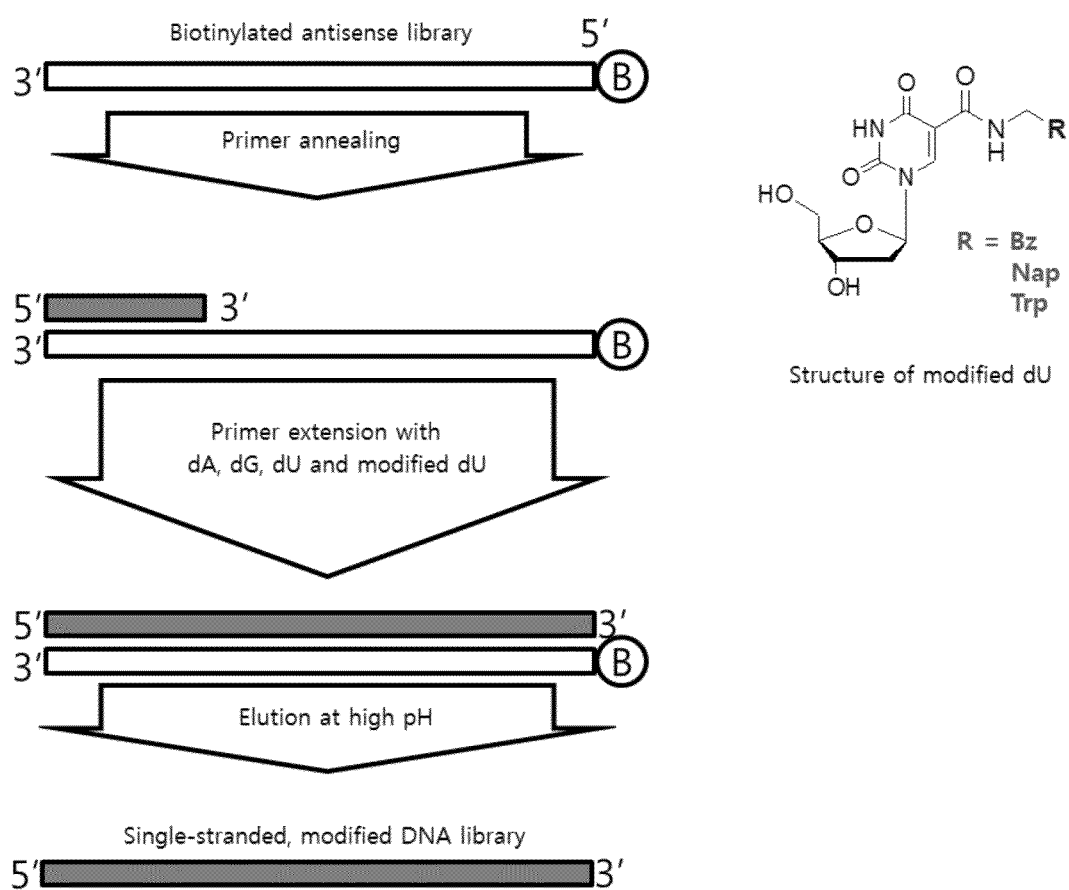
FIG. 1 is a schematic view illustrating a process of synthesizing an antisense library with a modified base (dUTP).

The present invention aims to provide an ERBB2 aptamer which highly specifically binds to Her2 protein, which is involved in the onset and metastasis of cancer, thereby suppressing the onset and metastasis of cancer or allowing for the diagnosis of cancer, and an anti-metastatic agent of cancer, comprising the same as an active ingredient.

Contemplated according to an aspect of the present invention are an ERBB2 aptamer which acts to block the EGF (Epidermal Growth Factor)- or HRG (heregulin)-mediated hetero-dimerization of EGFR (Epidermal Growth Factor Receptor)-ERBB2 or ERBB2-ERBB3 and the cancer survival-related downstream signaling pathway such as in AKT (RAC-alpha serin/threonine-protein kinase) and ERK (Extracellular signal-regulated kinase), an anti-cancer agent or a cancer diagnostic composition comprising the same as an active ingredient, and a method for suppressing oncogenesis or metastasis or for diagnosing cancer using the same.

The ERBB2 may be originated from mammals, preferably from humans, and may be of, for example, Accession No. P04626, P70424, P06494, O18735, or Q60553 (ERBB2_human).

The ERBB2 aptamer comprises 20 to 100 bases (nucleotides), preferably of 25 to 100 bases, e.g., 40 to 100 bases or 40 to 80 bases, some of which is modified, and is characterized by specific affinity to ERBB2. Other than the modified bases (nucleotides), the bases comprised in the ERBB2 aptamer of the present invention are selected from the group consisting of A, G, C, T, and deoxy forms thereof unless otherwise stated.

As used herein, the term "modified base" refers to dUTP (deoxyuracil) wherein the 5' position thereof is substituted with a hydrophobic functional group. The hydrophobic functional group may be selected from among a benzyl group, a naphthyl group, a pyrrolebenzyl group, tryptophan, and a combination thereof. Like this, the modification of dUTP bases at position 5' advantageously brings about a remarkable improvement in affinity for ERBB2, compared to the non-modified aptamer.

In the ERBB2 aptamer, the modified base may range in number from 5 to 15, and preferably from 7 to 13.

The ERBB2 aptamer of the present invention may be comprised of a total of 40 to 100 bases, and preferably 40 to 80 bases, and may be selected from the group consisting of the nucleotide sequences set forth in SEQ ID NOS:1 to 35.

In one embodiment, the ERBB2 aptamer is selected from the group consisting of nucleotide sequences set forth in SEQ ID NOS: 1 to 35, or optionally may further include 15 to 30 bases (nucleotides) at either or both of 5' and 3' termini of the nucleotide sequence selected from the group consisting of SEQ ID NOS: 1 to 35. For instance, the ERBB2 aptamer may comprise GGCTGGTGGTGTGGCTG (SEQ ID NO: 40) or GAGTGACCGTCTGCCTGA (SEQ ID NO: 39) at the 5' terminus of the nucleotide sequence selected from the group consisting of SEQ ID NOS: 1 to 5, and CAGGCAGACGGTCACTC (SEQ ID NO: 41) or CAGCCACACCACCAGCC (SEQ ID NO: 42) at the 3' terminus thereof, but is not limited thereto.

For serum stability, the ERBB2 aptamer may be optionally or additionally modified at either or both of the 5' and 3' termini (Examples 3 and 4). The modification may be achieved by conjugating at least one selected from the group consisting of PEG (polyethylene glycol), idT (inverted deoxythymidine), LNA (Locked Nucleic Acid), 2'-methoxy nucleoside, 2'-amino nucleoside, 2'F-nucleoside, an amine linker, a thiol linker, and a cholesterol, to either or both of the 5' and 3' terminus of the aptamer. In one preferred embodiment, the ERBB2 aptamer may be conjugated with either or both of PEG (polyethylene glycol; e.g., Mw. 500-50,000 Da) at the 5' terminus and idT (inverted deoxythymidine) at the 3' terminus.

'idT (inverted deoxythymidine)' is one of the molecules that are designed to protect susceptible aptamers against nuclease degradation. Typically, a nucleotide sequence consists of nucleotide units bonded to each other via a linkage between 3'-OH of a nucleotide building block and 5'-OH of a subsequent nucleotide building block. In contrast, idT forms a linkage between its 3'-OH and 3'-OH of an antecedent unit to externally expose 5'-OH, but not 3'-OH, thereby protecting the modified aptamer against 3'-exonuclease degradation.

The EGFR family is composed of four isotypes (EGFR1, ERBB2, ERBB3, ERBB4). ERBB2, unlike the general structure of the other three isotypes, lacks an extracellular domain responsible for binding with a ligand, such as EGF, NRG, and TGF-alpha, and thus may be in an activated state constitutively. When bound by EGF in normal cells, EGFR1 undergoes a structural change, which may lead to pairing with ERBB2 to create an activated heterodimer which, in turn, stimulates the intrinsic tyrosine kinase activity, thus triggering the intracellular signaling pathway. However, the clustering of EGFRs is different in specific cancer cells, such as breast cancer cells, colorectal cancer cells, etc. When stimulated in such cancer cells, ERBB2 receptors; which are ligand-less receptors in a constitutively activated state; form a homodimer, but not by way of other receptors such as EGFR1, ERBB3, etc., which results in an increase in their intrinsic tyrosine kinase activity, provoking the growth and metastasis of cancer cells.

The present invention will give the evidence that the ERBB2 aptamer blocks the dimerization of ERBB2, and exhibits an anti-tumor effect in vivo (Examples 2 and 4). By way of example, the ERBB2 aptamer according to the present invention may bind to the extracellular domain of ERBB2.

The EGFR family is composed of four isotypes (EGFR1, ERBB2, ERBB3, ERBB4). ERBB2, unlike the general structure of the other three isotypes, lacks an extracellular domain responsible for binding with a ligand, such as EGF, NRG, and TGF-alpha, and thus may be in an activated state constitutively. When bound by EGF in normal cells, EGFR1 undergoes a structural change, which may lead to pairing with ERBB2 to create an activated heterodimer which, in turn, stimulates the intrinsic tyrosine kinase activity, thus triggering the intracellular signaling pathway. However, the clustering of EGFRs is different in specific cancer cells, such as breast cancer cells, colorectal cancer cells, etc. When stimulated in such cancer cells, ERBB2 receptors, which are ligand-less receptors in a constitutively activated state, form a homodimer, but not by way of other receptors such as EGFR1, ERBB3, etc., which results in an increase in their intrinsic tyrosine kinase activity, provoking the growth of cancer cells.

In the present invention, aptamers which can bind to ERBB2, which accounts for oncogenesis and cancer metastasis, were excavated, and ERBB2 inhibitors were screened from the binding aptamers in the following manner. First, the A431 skin carcinoma cell line was selected to conduct the screening of ERBB2 inhibitors therein because it is found to express EGFR at a higher level, compared to other cancer cell lines. In addition, the activity of EGFR increases with the treatment of up to 16 nM of EGF, and peaks upon treatment for 5 min.

Further, the ERBB2 aptamers were found to be safe without abnormalities, as analyzed by an in vivo assay (Example 5). In detail, when ICR lineage male and female mice were intravenously injected with single doses thereof, the ERBB2 aptamers according to the present invention were estimated to have an approximate lethal dose (ALD) of more than 1,000 mg/kg for female mice, and a median lethal dose (LD$_{50}$) of 1215.8 mg/kg for male mice. In addition, even after repetitive intravenous injections for two weeks, no abnormalities were observed in terms of approximate toxicity in the ICR lineage male and female mice. Hence, the ERBB2 aptamer according to the present invention can be usefully applied to inhibition against cancer growth.

In accordance with another aspect thereof, the present invention addresses a pharmaceutical composition for the treatment of cancer or the suppression of metastasis of cancer, comprising the ERBB2 aptamer as an active ingredient.

The pharmaceutical composition of the present invention may be formulated into a variety of oral or parenteral dosage forms. For oral administration, for example, the pharmaceutical composition may be prepared into tablets, pills, hard or soft capsules, liquids, suspensions, emulsions, syrups, granules, and elixirs. These oral formulations may comprise a pharmaceutically acceptable excipient, including a diluent such as lactose, dextrose, sucrose, mannitol, sorbitol, cellulose, and/or glycine, and a lubricant such as silica, talc, stearic acid and magnesium or calcium salt thereof, and/or polyethylene glycol, in addition to the active ingredient.

As for a tablet, it may contain a binder, such as magnesium aluminum silica, starch paste, gelatin, tragacanth, methyl cellulose, sodium carboxy-methyl cellulose, and/or polyvinyl pyrrolidone. As needed, it may contain a disintegrant such as starch, agar, and alginic acid or sodium salt thereof, an effervescent mixture and/or absorbent, a colorant, a flavorant, or a sweetener.

Alternatively, the pharmaceutical composition may be formulated into parenteral dosage forms which may be administered via, for example, subcutaneous, intramuscular or intrathoracic routes. For use in parenteral administration, injections may be prepared by mixing the aptamer of the present invention with a stabilizer or buffer in water to give solutions or suspensions which are packaged in unit dosages such as ampules or vials.

The pharmaceutical composition of the present invention may be sterilized or may contain an auxiliary agent such as a preservative, a stabilizer, a wettable powder or emulsion promoter, an osmotic pressure-regulating salt, a buffer, etc., and/or a therapeutically useful agent, and may be formulated according to a typical method such as mixing, granulation or coating.

The pharmaceutical composition of the present invention may contain the active ingredient, that is, the ERBB2 aptamer, in an amount corresponding to the daily dose of 0.1 to 500 mg/kg (weight), preferably 0.5 to 100 mg/kg (weight), and may be administered once a day or divided into two or more daily doses via an oral or non-oral route.

So long as it is related to ERBB2, any cancer may be a target of the pharmaceutical composition of the present invention for the treatment of cancer or the suppression of cancer metastasis. For example, the cancer may be selected from the group consisting of breast cancer, colorectal cancer, lung cancer, gallbladder cancer, pancreatic cancer, and stomach cancer.

The subject to which the pharmaceutical composition of the present invention can be administered may be mammals, preferably rodents and humans.

In accordance with a further aspect thereof, the present invention addresses a method for treating cancer or suppressing cancer metastasis, comprising administering a therapeutically effective amount of the ERBB2 aptamer to a subject in need thereof. This method may further comprise identifying whether the subject is in need of cancer treatment, prior to the administration of the ERBB2 aptamer. As used herein, the term "therapeutically effective amount" refers to a dose that elicits a therapeutic effect from the subject administered. The therapeutically effective amount may vary depending on various factors including patient's condition, disease severity, etc., and may range, for example, from 0.1 to 500 mg/kg (weight), and preferably from 0.5 to 100 mg/kg (weight) per day. It may be administered once a day or may be divided into two or more doses.

In accordance with a still further aspect thereof, the present invention provides the use of the ERBB2 aptamer in cancer treatment or suppression against cancer metastasis. Also, the present invention provides the use of ERBB2 aptamer in cancer diagnosis.

In the method or the use, administration routes, patients (subjects), and kinds of cancer to be treated are as stated above.

Because ERBB2 is overexpressed in various cancers including breast cancer and colorectal cancer, the ERBB2 aptamer can be used as an active ingredient in the cancer diagnosis composition.

Still another aspect of the present invention envisages a method of providing information for cancer diagnosis.

The method of providing information for cancer diagnosis comprises:

preparing a biological specimen of a subject;

reacting the biological specimen with the ERBB2 aptamer; and measuring a binding level of the ERBB2 aptamer in the biological specimen, wherein when the biding level of the ERBB2 aptamer in the biological sample is higher than that in a normal specimen, the subject is determined as a cancer patient. Hence, the method may further comprise measuring a binding level of the ERBB2 aptamer in the normal specimen.

As used herein, the subject means a target to be determined for oncogenesis or cancer metastasis, and may be a mammal; preferably a rodent or a human.

So long as it is related to ERBB2, any cancer may be used in the method of providing information for cancer diagnosis. For example, the cancer may be at least one selected from the group consisting of breast cancer, colorectal cancer, lung cancer, gallbladder cancer, pancreatic cancer, and stomach cancer.

The normal specimen may originate from mammals, preferably including rodents and humans; and means a biological specimen obtained from a subject that is free of the generation and metastasis of the target cancer, for example, cancer selected from among breast cancer, colorectal cancer, lung cancer, gallbladder cancer, pancreatic cancer and stomach cancer.

The biological specimen may be such an isolate from mammals, whether including humans, as a cell, a tissue, blood, human fluid, saliva, etc.

For measuring the binding level of the ERBB2 aptamer in a biological specimen, a typical technique used to measure DNA aptamer binding in the art may be employed. For example, a fluorescent or radioactive label, after being conjugated to the terminus of the ERBB2 aptamer, may be used to quantify the binding level in a spectrophotometric or radiometric manner, but is not intended to limit the present invention.

Figure 2A:
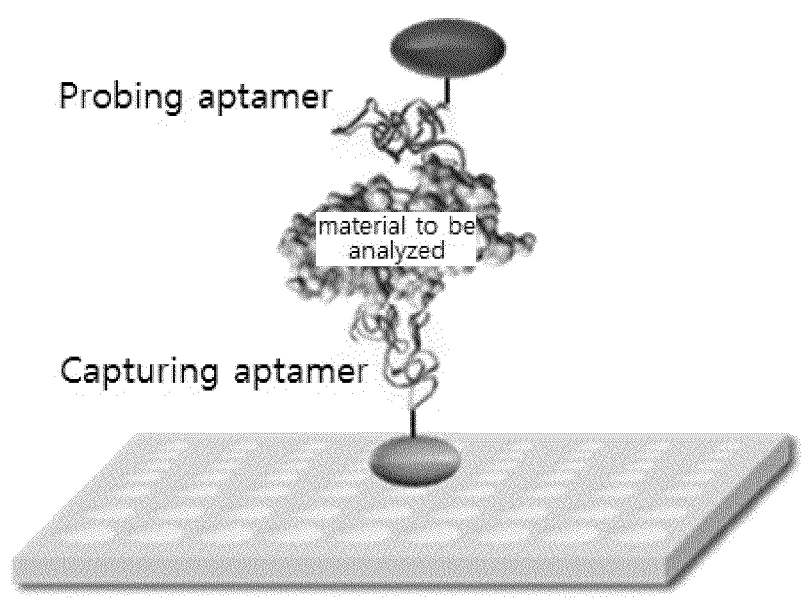
FIG. 2A schematically shows a sandwich assay using the ERBB2 aptamer of the present invention.

In one embodiment, selection is made of two ERBB2 aptamers which do not interfere with binding to ERBB2 because they are different in the biding site of ERBB2. One (the capture aptamer) is immobilized on a plate while the other (the detection aptamer) is labeled at its end with a fluorescent or radioactive material (or with a substance reacting with a fluorescent or radioactive material). Intensities of the fluorescent or radio signal allow for knowing the presence or overexpression of ERBB2 in the specimen (FIG. 2A).

Figure 2B:
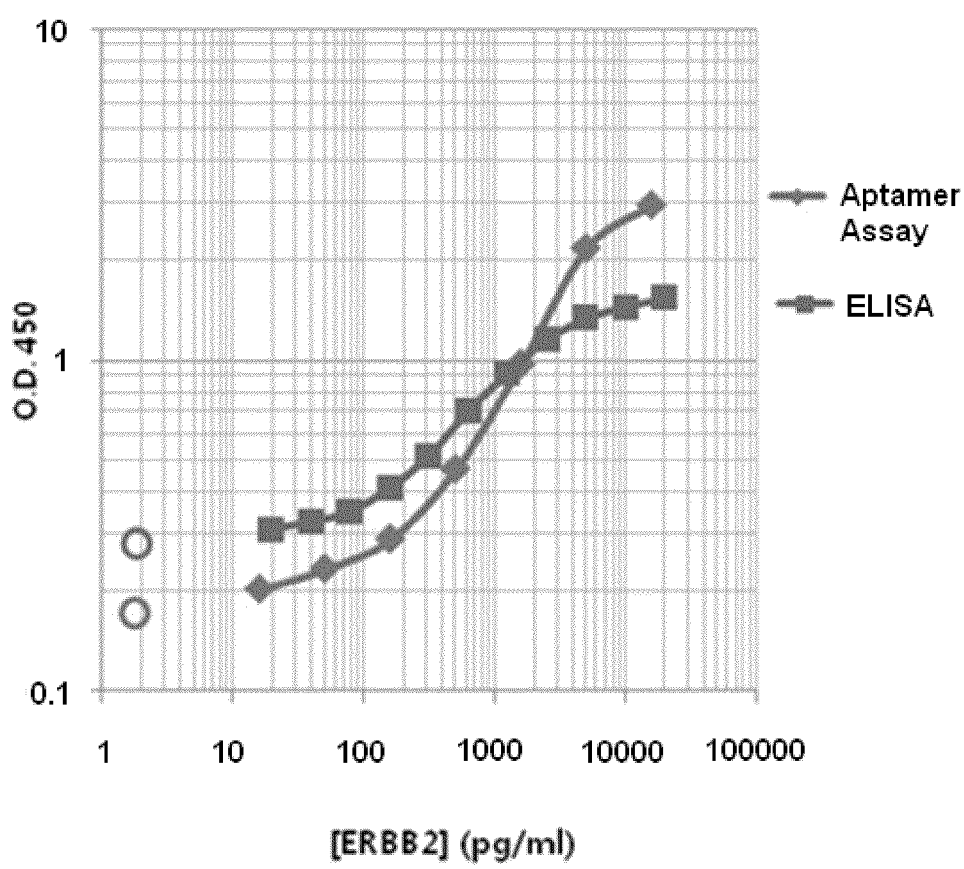
FIG. 2B shows analysis results obtained by the assay using the ERBB2 aptamer of the present invention, compared to those obtained by ELISA

Like this, the aptamers of the present invention can detect the existence or overexpression of ERBB2 in the specimen at remarkably high sensitivity, compared to conventional antibodies (FIG. 2B).

As described hereinbefore, the present invention provides an aptamer which is effectively inhibitory of ERBB2 and which is thus useful for the diagnosis, treatment and/or metastasis suppression of any ERBB2-related cancer.

EXAMPLES

A better understanding of the present invention may be obtained through the following examples which are set forth to illustrate, but are not to be construed as limiting the present invention.

Example 1

Excavation of ERBB2 Aptamer 1.1: Construction of Modified Nucleic Acid Library

For use in constructing a single-stranded modified DNA library necessary for SELEX, an antisense library biotinylated at 5' terminus [5'-Biotin-d (GGCTGGTGGTGTG-GCTG-N40-CAGGCAGACGGTCACTC)-3; (SEQ ID NO: 36)] was synthesized. The procedure was conducted as illustrated in the scheme of FIG. 1.

The antisense library was incubated with 0.5 mM dNTP (ATP, GTP, CTP, NapdUTP) I the presence of 20 µM 5' primer (GAGTGACCGTCTGCCTG; SEQ ID NO: 39) in 10× extension buffer (1.2M Tris-HCl pH7.8, 100 mM KCl, 60 mM $(NH_4)_2SO_4$, 70 mM $MgSO_4$, 1% Triton X-100, 1 mg/ml BSA) containing 0.25 U/ul KOD XL (KOD XL DNA polymerase, Novagen) at 70° C. for 1 hr to give double strand DNA.

After eluting with 20 mM NaOH, the eluate was neutralized with 80 mM HCl to afford a single-strand modified DNA library. This DNA library was concentrated using Amicon ultra-15 (Millipore) and quantitatively analyzed by UV spectrophotometry.

1.2: Excavation of Aptamer for ERBB2 Protein by SELEX

SELEX was used to select DNA aptamers binding to ERBB2 (R&D systems, 1129-ER-050).

Binding to ERBB2:

1 nmole of the synthesized library was incubated in selection buffer (200 mM HEPES, 510 mM NaCl, 25 mM KCl, 25 mM $MgCl_2$) for 5 min at 95° C., 70° C., 48° C., and 37° C., each. For negative selection, the library solution was mixed with 10 µL of 10× protein competition buffer (10 µM prothrombin, 10 µM casein, 0.1% (w/v) HSA (human serum albumin, SIGMA) and then incubated with Hexa-His-coated Talon beads (50% (w/v) slurry, 10 mg/ml Invitrogen) at 37° C. for 10 min.

After the negative selection, only the supernatant was transferred to a fresh tube and reacted at 37° C. for 1 with Talon beads on which ERBB2 was already immobilized. DNA-ERBB2 complex-bound Talon beads were washed five times with 100 µL of selection buffer (200 mM HEPES, 510 mM NaCl, 25 mM KCl, 25 mM $MgCl_2$). For the fifth round, the beads were washed just after being transferred to a new plate. The target-bound library was eluted with bound 85 µL of 2 mM NaOH, followed by neutralization with 20 µL of an 8 mM HCl solution.

Amplification:

Target-bound library DNA was amplified by QPCR (quantitative PCR, IQ5 multicolor real time PCR detection system, Bio-rad). The primers used in the library construction, that is, 5' primer (GAGTGACCGTCTGCCTG (SEQ ID NO: 39) and 3' primer (Biotin-GGCTGGTGGTGTGGCTG, Biotin-(SEQ ID NO: 40)), each 5 uM (5×QPCR master Mix, Novagen), 0.075 U/ul KOD (Novagen) (? 임종 훈), 1 mM dNTP (Roche Applied science), 25 mM $MgCl_2$, and 5×SYBR green I (Invitrogen) were mixed to a final volume of 125 µL, and subjected to one thermal cycle of 96° C. for 15 sec, 55° C. for 10 sec, and 68° C. for 30 min, and then 30 thermal cycles of 96° C. for 15 sec, and 72° C. for 1 min to afford a double strand library.

eDNA Preparation:

eDNA, abbreviated for enzymatic DNA, refers to an aptamer, produced from a DNA template by a polymerase. The DNA library constructed by QPCR was immobilized on Myone SA beads by mixing with 25 µL of Myone SA beads (Invitrogen) at room temperature for 10 min. In this regard, the QPCR product was used in an amount of 60 ul. They were denatured to single-stranded DNA by use of 20 mM NaOH.

Thereafter, DNA having modified nucleic acids was synthesized in the same manner as in the library construction of Example 1.1 and used in a subsequent round. A total of 8 SELEX rounds were conducted. For more selective binding, the DNA/protein (ERBB2) complex was diluted 1/200 and 1/400 in 10 mM $DxSO_4$ (Sigma), and used in from round 4 to round 6, and in from round 7 to round 8, respectively.

Pool Binding Assay:

A filter binding assay was performed to examine the binding affinity of the DNA pool, obtained after the SELEX rounds, for ERBB2. The pools from SELEX rounds 6 and 8 were labeled at the termini with $\alpha$-$P^{32}$ ATP (Perkin Elmer) and TdT (terminal deoxynucleotidyl transferase, NEB). The library DNA 1 µM, obtained through the SELEX procedure, 0.25 µL $\alpha$-$P^{32}$ ATP (5 µM, Perkin Elmer), 0.25 µL TdT, and a reaction volume of 10 µL of 10×NEB buffer4 (NEB) were reacted at 37° C. for 30 min, followed by incubation at 70° C. for 10 mM to inactivate TdT. The labeled DNA pool was filtered using Micro spin G-50 column (GE healthcare).

The labeled DNA pool was added at a dose of 20,000 cpm to 100 µL of 1×SB buffer (200 mM HEPES, 510 mM NaCl, 25 mM KCl, 25 mM $MgCl_2$), and cooled slowly from 95° C. to 37° C. at a decreasing rate of 0.1° C. per second. A 12-point serial dilution of the ERBB2 protein (R&D systems, 1129-ER-050) was conducted from 100 nM in a buffer (200 mM HEPES, 510 mM NaCl, 25 mM KCl, 25 mM $MgCl_2$), and reacted with 30 µL of each of the heated and cooled DNA pools at 37° C. for 30 min. A nylon membrane (GE healthcare) was spotted with 2 µL of each DNA-ERBB2 mixture and then added with 5.5 µL of Zorbax resin (Agilent). It was added to a Durapore filter (Millipore) which was previously wetted with 50 µL of 1×SB buffer (200 mM HEPES, 510 mM NaCl, 25 mM KCl, 25 mM $MgCl_2$), followed by producing a vacuum. Then, the membrane filter was rinsed with 100 µL of 1× selection buffer (200 mM HEPES, 510 mM NaCl, 25 mM KCl, 25 mM $MgCl_2$). The filter plates were exposed overnight to image plates, and the images thus formed on the image plates were quantitatively analyzed using FLA-5100 (Fuji).

Binding affinity between the ERBB2 protein and the DNA pools obtained through the SELEX rounds is summarized in Table 1, below. The binding affinity was obtained from the results of the filter binding assay, using SigmaPlot 11 (Systat Software Inc.). In Table 1, $B_{Max}$ describes the ratio of bound aptamers to input aptamers while $K_d$ (dissociation constant) accounts for affinity.

TABLE 1

|   | Bz library | Trp Library | Nap Library | Group 1 | Group 2 | Group 3 | Group 4 | Group 5 |
|---|---|---|---|---|---|---|---|---|
| $B_{max}$ | 3.23E−11 | 1.32E−02 | 1.79E−02 | 0.23 | 0.26 | 0.22 | 0.51 | 0.36 |
| $K_d$ (nM) | 6500.86 | 1.19E−03 | 7.35E−03 | 0.56 | 21.86 | 10.41 | 7.34 | 61.76 |

In Table 1, the library refers to DNAs having random nucleotide sequences modified with a benzyl group, a tryptophan group, or a naphthyl group, and each Group means an ssDNA pool obtained after a predetermined SELEX round using a specific library: Group 1 stands for Nap Library 6R pool, Group 2 for Bz library 6R Pool, Group 3 for Nap library 8R pool, Group 4 for Trp library 8R pool, and Group 5 for Bz library 8R pool.

Base Sequencing of ERBB2 Aptamer:

Since Group 1, obtained after 6 SELEX rounds, was observed to exhibit the highest binding affinity, it was amplified by QPCR, as described above, to give a double-stranded DNA. This QPCR product was cloned using a TA cloning kit (SolGent), followed by base sequencing using the M13 primer (CAGGAAACAGCTATGAC) present on the vector to identify the following sequences.

The DNA aptamers specifically binding to ERBB2 have the nucleotide sequences as set forth in 5'-GAGTGAC-CGTCTGCCTG-[Core sequence]-CAGCCACACCAC-CAGCC-3' in which the core sequence is as given in Table 2, below. In Table 2, '6' represents Naphthyl-dU.

TABLE 2

| # | Description (Clone No.) | Core sequence |
|---|---|---|
| 1 | 9-ER-N-A01_A05 | A6G66AGAG666GCC6GAG6GCC6CG6AAGGGCG6AACAA (SEQ ID NO: 1) |
| 2 | 9-ER-N-A02_B05 | 6AC6GGGCCCG66AGCC6C6GGCGC6CC66CGC66G6GCC (SEQ ID NO: 2) |
| 3 | 9-ER-N-A03_C05 | 66A6CAACGCAC6GAGGGCG6CAGC66C66666AGG (SEQ ID NO: 3) |
| 4 | 9-ER-N-A04_D05 | A6G66AGAG666GCC6GAG6GCC6CGCAAGGGCG6AACAG (SEQ ID NO: 4) |
| 5 | 9-ER-N-A06_E05 | 6CC6G6CCCGG666ACACAAG66AAGGCAGCCGC6GGA6A (SEQ ID NO: 5) |
| 6 | 9-ER-N-B02_F05 | G6C6GAACACCGAGA66AGC6GAACGAACGG6A6GGACG6 (SEQ ID NO: 6) |
| 7 | 9-ER-N-B03_G05 | 6CC6GGCA6G66CGA6GGAGGCC666GA66ACAGCCCAGA (SEQ ID NO: 7) |
| 8 | 9-ER-N-B04_H05 | CGCGA66AGA6GAACGCACAA6ACCCG66C6GAG6AAAG6 (SEQ ID NO: 8) |
| 9 | 9-ER-N-B08_A06 | G6C6GAACACCGAGA66AGCCGAACGAACGG6A6GGACG6 (SEQ ID NO: 9) |
| 10 | 9-ER-N-B09_B06 | G66AGAC6GAACGCAC6GAGGGCCGCAGCC6A6C6GAAGG (SEQ ID NO: 10) |
| 11 | 9-ER-N-B12_C06 | A6G66AGAG666GCC6GAG6GCC6CGCAAGGGCG6AACAA (SEQ ID NO: 11) |
| 12 | 9-ER-N-C02_D06 | 6CC6GGCA6G66CGA6GGAGGCC666GA66ACAGCCCAGA (SEQ ID NO: 7) |
| 13 | 9-ER-N-C03_E06 | G6C6GAGCA6CGCG666AGCCGAACGC6CGG6GAGG6AGA6 (SEQ ID NO: 12) |
| 14 | 9-ER-N-C05_F06 | 6CA6GGCA6G66CGA6GGAGGCC666GA66ACAGCCCAGA (SEQ ID NO: 13) |
| 15 | 9-ER-N-C06_G06 | C6ACACGAA6CAAC6CCCC6CCGCA6AC6GAACA6CACAA (SEQ ID NO: 14) |
| 16 | 9-ER-N-C08_H06 | 66AGCAAAA6GCCA6G6GCG6CC6G6CCCGG666ACAGC (SEQ ID NO: 15) |
| 17 | 9-ER-N-C10_A07 | 6GA6G6CCCCAAC6CAGC6G6GAA6C6A6GCCCCCGCCCA (SEQ ID NO: 16) |
| 18 | 9-ER-N-D01_B07 | C6GAGCGG66AC6ACACCACCG6GAGACC66AG66ACAAA (SEQ ID NO: 17) |
| 19 | 9-ER-N-D02_C07 | A66AGA6GAAAGCGCA66CCAACAACAGA6AA6C6GAGGG (SEQ ID NO: 18) |
| 20 | 9-ER-N-D03_D07 | 6CC6GGCA6G66CGA6GGAGGCC666GA66ACAGCCCAGA (SEQ ID NO: 7) |
| 21 | 9-ER-N-D04_E07 | 666GGAG6G6C66ACGG66GGAG6AA6CGAGGA6GGA6GA (SEQ ID NO: 19) |
| 22 | 9-ER-N-D05_F07 | CCG66ACC6ACC6CC6CGACCG6GGG6GCCC66AG6CCCA (SEQ ID NO: 20) |
| 23 | 9-ER-N-D06_G07 | 6CC6GGCA6G66CGA6GGAGGCC666GA66ACAGCCAGA (SEQ ID NO: 21) |
| 24 | 9-ER-N-D07_H07 | CCG66ACC6ACC6CC6CGACCG6GGG6GCC666AG6CCCA (SEQ ID NO: 22) |
| 25 | 9-ER-N-D09_A08 | A6G66AGAG666GCC6GAG6GCC6CGCAAGGGCG6AACAA (SEQ ID NO: 23) |
| 26 | 9-ER-N-D11_B08 | 6CC6GGCA6G66CGA6GGAGGCC666GA66ACAGCCCAG6 (SEQ ID NO: 24) |

TABLE 2-continued

| # | Description (Clone No.) | Core sequence |
|---|---|---|
| 27 | 9-ER-N-E02_C08 | CCG66ACC6ACC6CC6CGACCG6GGG6GCCC66AG6CCCA (SEQ ID NO: 20) |
| 28 | 9-ER-N-E04_D08 | A66AGA6GAAAGCACA66CCAACAACAGA6AA6C6GAGGG (SEQ ID NO: 25) |
| 29 | 9-ER-N-E09_E08 | 6CC6GGCA6G66CGA6GGAGGCC666GA66ACAGCCCAGA (SEQ ID NO: 7) |
| 30 | 9-ER-N-E11_F08 | A6G66AGAG666GCC6GAG6GCG6CGCAAGGGCG6AACAG (SEQ ID NO: 26) |
| 31 | 9-ER-N-E12_G08 | 6GAGAAGGGC6G6GCC66AC6CAAAA666GGGA6C6GAA (SEQ ID NO: 27) |
| 32 | 9-ER-N-F01_H08 | G66AGAC6GAACGCAC6GAGGGCCGCAGCC6A6C6GAAGG (SEQ ID NO: 10) |
| 33 | 9-ER-N-F02_A09 | G6C6GAACACCGAGA66AGCCGAACGAACGG6A6GGACG6 (SEQ ID NO: 9) |
| 34 | 9-ER-N-F03_B09 | G6C6GAACACCGAGA66AGCCGAACGAACGG6A6GGACG6 (SEQ ID NO: 9) |
| 35 | 9-ER-N-F04_C09 | G6C6GAACACCGAGA66AGCCGAACGAACGG6A6GGACG6 (SEQ ID NO: 9) |
| 36 | 9-ER-N-F05_D09 | 6CC6GG6A6G66CGA6GGAGGCC666GA66ACAGCCCAGA (SEQ ID NO: 28) |
| 37 | 9-ER-N-F08_E09 | 6AGA6C6C6GA66AGG6AGAACGCCC6AC6C6AACGGCAG (SEQ ID NO: 29) |
| 38 | 9-ER-N-F09_F09 | 6GAGAAGGGC6G6GCC66AC6CAAAA666GGGGA6C6GAA (SEQ ID NO: 30) |
| 39 | 9-ER-N-F11_G09 | 6GAGAAGGGC6G6GCC66AC6CAAAA666GGGGA6C6GAA (SEQ ID NO: 31) |
| 40 | 9-ER-N-G02_H09 | A66AGA6GAAAGCGCA66CCAACAACAGA6AA6C6GAGGG (SEQ ID NO: 18) |
| 41 | 9-ER-N-G03_A10 | G6C6GAACACCGAGA66AGCCGAACGAACGG6A6GGACG6 (SEQ ID NO: 9) |
| 42 | 9-ER-N-G04_B10 | CG6CC66GG6GAG666GGG6C6GAGCAGGAGCACG6GAG6 (SEQ ID NO: 32) |
| 43 | 9-ER-N-G08_C10 | 6CC6GGCA6G66CGA6GGAGGCC666GA66ACAGCCCAGA (SEQ ID NO: 7) |
| 44 | 9-ER-N-G09_D10 | G6C6GAACACCGAGA66AGCCGAACGAACGG6A6GGACG6 (SEQ ID NO: 9) |
| 45 | 9-ER-N-H01_E10 | A66AGA6GAAAGCACA66CCAACAACAGA6AA6C6GAGGG (SEQ ID NO: 33) |
| 46 | 9-ER-N-H02_F10 | 6CC6GGCA6G66CGA6GGAGGCC666GA66ACAGCCCAGA (SEQ ID NO: 7) |
| 47 | 9-ER-N-H03_G10 | A66AGA6GAAAGCACA66CCAACAACAGA6AA6C6GAGGG (SEQ ID NO: 34) |
| 48 | 9-ER-N-H04_H10 | G66AGAC6GAACGCAC6GAGGGCCGCAGCC6A6C6GAAGG (SEQ ID NO: 10) |
| 49 | 9-ER-N-H08_A11 | 6CC6GGCA6G66CGA6GGAGGCC666GA66ACAGCCCAGA (SEQ ID NO: 7) |
| 50 | 9-ER-N-H09_B11 | A6G66AGAG6C6GCC6GAG6GCC6CGCAAGGGCG6AACAG (SEQ ID NO: 35) |

6 = NapdU [5-(N-Naphthylcarboxyamide)-2'-deoxyuridine]

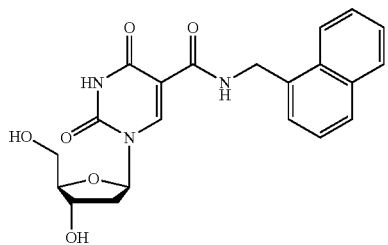

A = 2'-deoxyAdenosine
G = 2'-deoxyGuanosine
C = 2'-deoxyCytidine
T = 2'-deoxyThymidine(Thymidine)

The excavated ERBB2 aptamers were categorized into similar families as follows (sequence homology was based on 85% identity on a nucleotide level):

TABLE 3

74.00% (37/50) Multi-Copy

| # | Description | The number | (%) | |
|---|---|---|---|---|
| [1] | 9-ER-N-A01_A05 | 5 | 10.00 | A6G66AGAG666GCC6GAG6 GCC6CG6AAGGGCG6AACAA (SEQ ID NO: 1) [1, 11, 25, 30, 50] |
| [10] | 9-ER-N-B09_B06 | 3 | 6.00 | G66AGAC6GAACGCAC6GAG GGCCGCAGCC6A6C6GAAGG (SEQ ID NO: 10) [10, 32, 48] |
| [12] | 9-ER-N-C02_D06 | 11 | 22.00 | 6CC6GGCA6G66CGA6GGAG GCC666GA66ACAGCCCAGA (SEQ ID NO: 7) [7, 12, 14, 20, 23, 26, 29, 36, 43, 46, 49] |
| [19] | 9-ER-N-D02_C07 | 5 | 10.00 | A66AGA6GAAAGCGCA66CC AACAACAGA6AA6C6GAGGG (SEQ ID NO: 18) [19, 28, 40, 45, 47] |
| [22] | 9-ER-N-D05_F07 | 3 | 6.00 | CCG66ACC6ACC6CC6CGAC CG6GGG6GCCC66AG6CCCA (SEQ ID NO: 20) [22, 24, 27] |
| [31] | 9-ER-N-E12_G08 | 3 | 6.00 | 6GAGAAGGGC6G6GCC66AC 6CAAAA666GGGA6C6GAA (SEQ ID NO: 27) [31, 38, 39] |
| [33] | 9-ER-N-F02_A09 | 7 | 14.00 | G6C6GAACACCGAGA66AGC CGAACGAACGG6A6GGACG6 (SEQ ID NO: 9)[6, 9, 33, 34, 35 41, 44] |

For #12 clone (9-ER-N-C02_D06), the same nucleotide sequence was repeated 11 times out of 50 sequences. Then, the same nucleotide sequence was repeated 7 times for #33 (9-ER-N-F02_A09), 5 times for #1(9-ER-N-A01_A05), five times for 19 (9-ER-N-D02_C07), and three times for #10 (9-ER-N-B09_B06).

Sequence similarities on the excavated ERBB2 aptamers were identified by measuring repeated nucleotide sequence regions among clones, and their frequencies, and the results are given as follows:

```
86.00% (43/50) Families
[10] 9-ER-N-B09_B06 Count: 3 0.06%
G66AGAC6GAACGCAC6GAGGGCCGCAGCC6A6C6GAAGG
       ***************         *******
................................A6C6GAA..  Pattern_1 x 18 times
........AACGCAC6GAGGGC...................  Pattern_6 x 4 times
.......6GAACGCAC.........................  Pattern_10 x 9 times
                                            Score: 31

[33] 9-ER-N-F02_A09 Count: 7 0.14%
G6C6GAACACCGAGA66AGCCGAACGAACGG6A6GGACG6
*******        ***********
A6C6GAA..................................  Pattern_1 x 18 times
................66AGCCGAACG..............  Pattern_2 x 7 times
                                            Score: 25

[31] 9-ER-N-E12_G08 Count: 3 0.06%
6GAGAAGGGC6G6GCC66AC6CAAAA666GGGA6C6GAA
          *******        *******
.............................A6C6GAA       Pattern_1 x 18 times
..............CC66AG6....................  Pattern_4 x 7 times
                                            Score: 25

[19] 9-ER-N-D02_C07 Count: 5 0.10%
A66AGA6GAAAGCGCA66CCAACAACAGA6AA6C6GAGGG
*********                       *******
...............................A6C6GAA...  Pattern_1 x 18 times
A66AGA6GAA...............................  Pattern_11 x 7 times
                                            Score: 25

[8] 9-ER-N-B04_H05 Count: 1 0.02%
CGCGA66AGA6GAACGCACAA6ACCCG66C6GAG6AAAG6
              **************
..........6GAACGCAC......................  Pattern_10 x 9 times
....A66AGA6GAA...........................  Pattern_11 x 7 times
                                            Score: 16

[16] 9-ER-N-C08_H06 Count: 1 0.02%
66AGCAAAA6GCCA6G6GCG6CC6G6CCCGG666ACAGC
                      ******************
..............................66ACAGC      Pattern_3 x 12 times
....................6CC6G6CCCGG666ACA...   Pattern_9 x 2 times
                                            Score: 14
```

-continued

[3] 9-ER-N-A03_C05 Count: 1 0.02%
66A6CAACGCAC6*GAGGGC***G6CAGC66C66666AGG
    ***************
....AACGCAC6GAGGGC.................... Pattern_6 x 4 times
..6GAACGCAC......................... Pattern_10 x 9 times
                                               Score: 13

[12] 9-ER-N-C02_D06 Count: 11 0.22%
6CC6GGCA6G66CGA6GGAGGCC666GA66ACAGCCCAGA
                               *******
..........................66ACAGC..... Pattern_3 x 12 times
                                               Score: 12

[4] 9-ER-N-A04_D05 Count: 1 0.02%
A6G6*AGAG66*6GCC6GAG6GCC6CGCAAGGGCG6AACAG
    **********************************
.....AGAG666GCC6GAG6GCC6CG............... Pattern_5 x 4 times
..........*AGAG666GCC6GAG6GCC6CGCAAGGGCG6*. Pattern_7 x 3 times
............6GCC6GAG6GCC6CGCAAGGGCG6AACAG Pattern_8 x 2 times
                                               Score: 9

[42] 9-ER-N-G04_B10 Count: 1 0.02%
CG6CC6 6GG6GAG666GGG6C6GAGCAGGAGCACG6GAG6
   *******
...CC6 6AG6.............................. Pattern_4 x times
                                                Score: 7

[22] 9-ER-N-D05_F07 Count: 3 0.06%
CCG66ACC6ACC6CCGCGACCG6GGG6GCCC6 6AG6CCCA
                            *******
.........................CC6 6AG6.... Pattern_4 x 7 times
                                                Score: 7

[18] 9-ER-N-D01_B07 Count: 1 0.02%
C6GAGCGG66AC6ACACCACCG6GAGACC6 6AG6 6ACAAA
                            *******
..........................CC6 6AG6...... Pattern_4 x 7 times
                                                Score: 7

[13] 9-ER-N-C03_E06 Count: 1 0.02%
G6C6GAGCA6CGCG666AGCCGAACGC6CGG6GAGG6AGA6
                **********
................66AGCCGAACG.............. Pattern_2 x 7 times
                                                Score: 7

[1] 9-ER-N-A01_A05 Count 5 0.10%
A6G66AGAG666GCC6GAG6GCC6CGGAAGGGCG6AACAA
    ********************
.....AGAG666GCC6GAG6GCC6CG............... Pattern_5 x 4 times
                                                Score: 4

[5] 9-ER-N-A06_E05 Count: 1 0.02%
6CC6G6CCCGG6 6ACACAAG66AAGGCAGCCGC6GGA6A
****************
6CC6G6CCCGG6 6ACA...................... Pattern_9 x 2 times
                                                Score: 2

10.00% (5/50) Orphans
[2] 9-ER-N-A02_B05 1 0.02%
6AC6GGGCCCG66AGCC6C6GGCGC6CC66CGC66G6GCC

[15] 9-ER-N-C06_G06 1 0.02%
C6ACACGAA6CAAC6CCCC6CCGCA6AC6GAACA6CACAA

[17] 9-ER-N-C10_A07 1 0.02%
6GA6G6CCCCAAC6CAGC6G6GAA6C6A6GCCCCCGCCCA

[21] 9-ER-N-D04_E07 1 0.02%
666GGAG6G6C66ACGG66GGAG6AA6CGAGGA6GGA6GA

[37] 9-ER-N-F08_E09 1 0.02%
6AGA6C6C6GA66AGG6AGAACGCCC6AC6C6AACGGCAG

Clone Binding Assay:

To examine the binding affinity of clones having the repeated base sequences, a filter binding assay was performed in a manner similar to that for the pool binding assay. This binding affinity was obtained from the data of the filter binding assay using SigmaPlot 11 (Systat Software Inc.), and the results are given in Table 4, below. In Table 4, $B_{Max}$ describes the ratio of bound aptamers to input aptamers, meaning higher performance with higher proximity to 1, while $K_d$ (dissociation constant) accounts for affinity, meaning higher affinity with lower values.

TABLE 4

|  | #12 | #33 | #11 | #19 | #10 | Group1 | Nap Library |
|---|---|---|---|---|---|---|---|
| Bmax | 0.33 | 0.03 | 0.29 | 0.37 | 0.25 | 0.19 | 0.06 |
| $K_d$ (nM) | 0.78 | 9.79 | 3.06 | 15.79 | 3.71 | 3.36 | 10.31 |

The assay was performed with a total of 5 kinds of clones, and of them, clone #12 (9-ER-N-C02_D06) was measured to have a $K_d$ of 0.78 nM, thus exhibiting high affinity for the target protein. For clone #11 (9-ER-N-B12_C06), good inhibition was detected against the target protein, as screened.

Determination of Optimal Aptamer Sequence by Truncation of Full-Length Aptamer:

The aptamers cloned through the SELEX procedure were around 80-mer long. Nucleotide sequences in this range of length were selected since they were observed to have suitable dissociation constants ($K_d$) with regard to the target protein. From the two best clones, clone #11 (labeled as 1194-2, SEQ ID NO: 37) and clone #12 (labeled as 1194-1, SEQ ID NO: 38), a full-length 74-mer aptamer, and aptamers 1194-35 (AP001-25, SEQ ID NO: 7) and 1194-34 (AP001-24, SEQ ID NO: 11), both having a random region 40-mer long, except for the primer region, were synthesized (Table 5).

ERBB2 Aptamer Synthesis:

Aptamers were in-house synthesized on tMermade 12 Synthesizer (Bioautomation), a kind of solid phase synthesizers, by solid phase oligonucleotide synthesis.

ERBB2 Aptamer Separation/Purification and QC:

The modified aptamers, excavated by the synthesis, filtration and identification of aptamers bearing modified nucleotides, were chemically synthesized from modified-dU-phosphoramidite on an oligonucleotide synthesizer (Mermade 12 from Bioautomation) by a phosphoramidite coupling reaction. After synthesis, the resin (200 nmole-dA (Bz) synthesis column, 1000 A (MM1-1000-2)) was immersed in t-butylamine: methanol: water (1:1:2 v/v/v) at 70° C. for 5 hrs so as to deprotect the synthesized aptamers, followed by drying in a vacuum. The aptamers were separated and purified by HPLC using a C18 column (Waters,)(bridge OST C18 10×50 mm), with a gradually increasing concentration gradient of acetonitrile flowing at a rate of 5 ml/min at 65° C.

Modified aptamers were successfully synthesized with a purity of 70~90%, as analyzed by chromatograms at UV UV 254 nm and 290 nm on HPLC. Exact molecular weights of them were measured using an LC-ESI MS spectrometer (Waters HPLC systems (Waters)+Qtrap2000(ABI)), and are given in Table 5, below.

TABLE 5

Sequences of ERBB2 aptamers (ERBB2 aptamer = NapdU-modified DNA aptamer, 6 = NapdU)

| Code # | Sequence (DNA) | Mw (g/mole) |
|---|---|---|
| #11 | GAGTGACCGTCTGCCTGA6G66AGAG666GCC6GAG6GCC6C GCAAGGGCG6AACAACAGCCACACCACCAGCC (SEQ ID NO: 37) | 24448.45 |
| #12 | GAGTGACCGTCTGCCTG6CC6GGCA6G66CGA6GGAGGCC66 6GA66ACAGCCCAGACAGCCACACCACCAGCC (SEQ ID NO: 38) | 24544.55 |
| AP001-24 #11 short | A6G66AGAG666GCC6GAG6GCC6CGCAAGGGCG6AACAA (SEQ ID NO: 11) | 14067.80 |
| AP001-25 #12 short | 6CC6GGCA6G66CGA6GGAGGCC666GA66ACAGCCCAGA (SEQ ID NO: 7) | 14163.90 |

11(1194-2): 9-ER-N-B12_C06,
12 (1194-1): 9-ER-N-C02_D06
6 = NapdU [5-(N-Napthykarboxyamide)-2'-deoxyuridine]
A = 2'-deoxyAdenosine
G = 2'-deoxyGuanosine
C = 2'-deoxyCytidine
T = 2'-deoxyThymidine(Thymidine)
The NapdU is representedby the following formula:

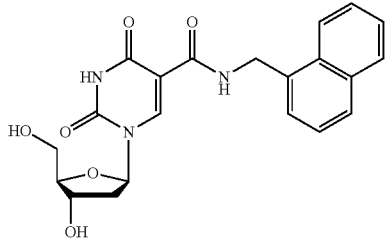

Molecular Weight Measurement of Synthesized ERBB2 Aptamer:

Using an LC-ESI MS spectrometer, aptamers and aptamer agents, having a molecular weight of 10,000 g/mole or higher, were measured for exact molecular weight within an error of 0.02%.

Sandwich Assay with ERBB2 Aptamer:

In order to examine the possibility that an assay for exactly measuring concentrations of ERBB2 in samples using the excavated ERRBB2 aptamers might be developed, ELISA was performed with the two aptamers AP001-24 (SEQ ID NO: 11) and AP001-25 (SEQ ID NO: 7), which bind to ERBB2, simultaneously, but without interference with each other, and succeeded in detecting purified ERBB2 in the presence of 5% serum (Sigma) In this regard, the aptamer AP001-25 was immobilized on the plate and conjugated at its terminus with biotin, followed by a coloring reaction with streptavidin-HRP (FIG. 2A). For comparison with an antibody, an assay was performed using the ERBB2 ELISA Kit of RnD Systems.

The results are given in FIG. 2B. As can be seen in FIG. 2B, the ERBB2 aptamers of the present invention allowed the sandwich assay to detect added ERBB2 (R&D systems, 1129-ER-050) on such a high sensitivity level as down to 50 pg/ml even in a complicated sample condition including 5% serum.

Example 2

Assay for In Vitro Efficacy of ERBB2 Aptamers 2.1: Screening of Excavated Aptamers for Blocking ERBB2 Signaling The EGFR family is composed of four isotypes (EGFR1, ERBB2, ERBB3, and ERBB4). ERBB2, unlike the general structure of the other three isotypes, lacks an extracellular domain responsible for binding with a ligand, such as EGF, NRG, and TGF-alpha, and thus may be in an activated state constitutively. When bound by EGF in normal cells, EGFR1 undergoes a structural change, which may lead to pairing with ERBB2 to create an activated heterodimer which, in turn, stimulates the intrinsic tyrosine kinase activity, thus triggering the intracellular signaling pathway. However, the clustering of EGFRs is different in specific cancer cells, such as breast cancer cells, colorectal cancer cells, etc. When stimulated in such cancer cells, ERBB2 receptors, which are ligand-less receptors in a constitutively activated state, form a homodimer, but not by way of other receptors such as EGFR1, ERBB3, etc., which results in an increase in their intrinsic tyrosine kinase activity, provoking the growth of cancer cells.

In the present invention, aptamers which can bind to ERBB2, which accounts for oncogenesis and cancer metastasis, were excavated, and ERBB2 inhibitors were screened from the binding aptamers in the following manner.

Figure 3A:
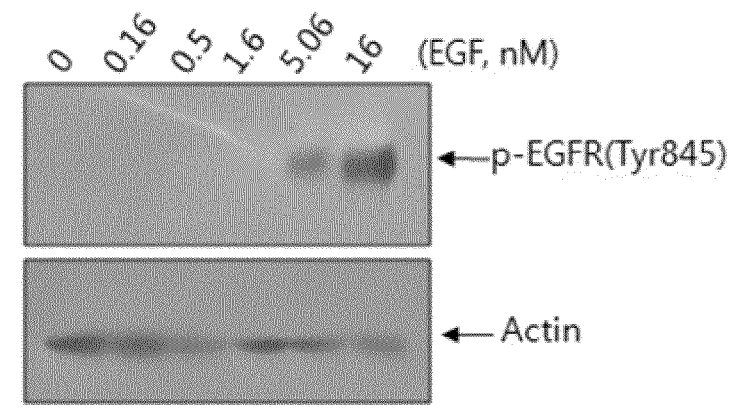
FIGS. 3A and 3B show changes in the tyrosine (Tyr845) phosphorylation of EGFR (ERBB2) with EGF concentration and time, respectively.
Figure 3A:
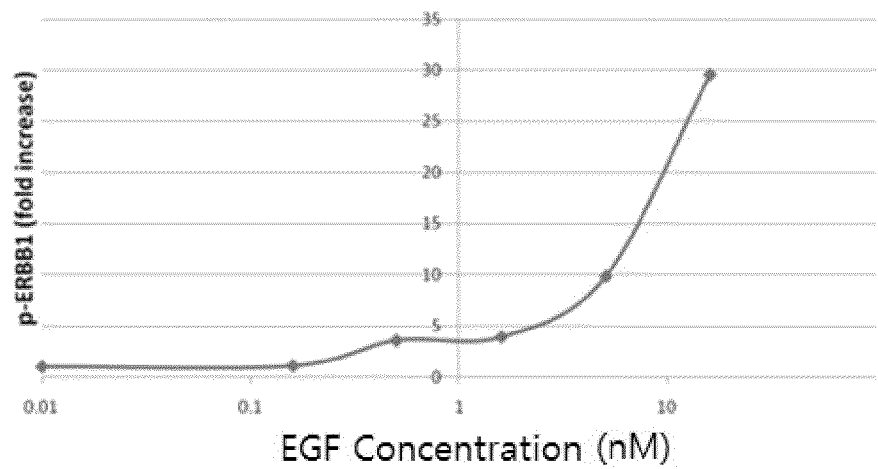
Figure 3B:
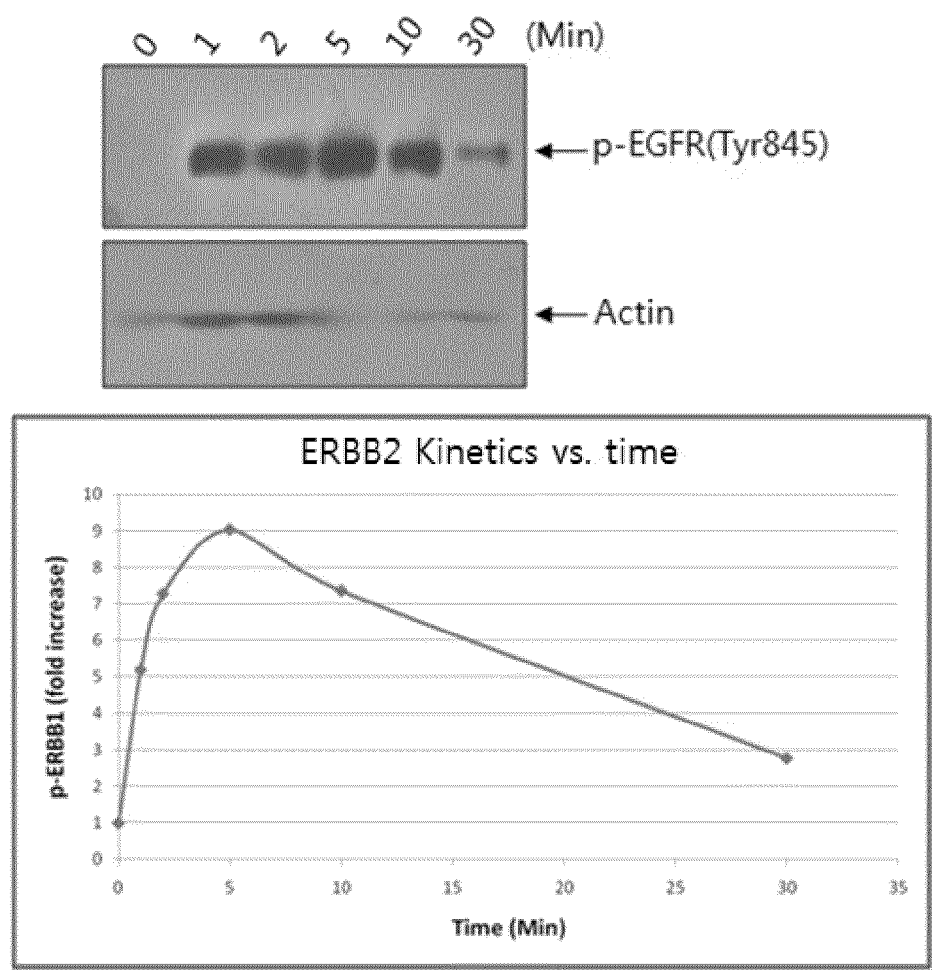

To monitor a change in the tyrosine (Tyr845) phosphorylation of EGFR with the concentration and treatment time of EGF, a cell line (A431, ATCC) was treated with various concentrations of EGF (P01133, Sigma) for 5 min (FIG. 3A), or with 10 nM EGF for various periods of time (FIG. 3B). After incubation in a lysis buffer (1% Triton X-100, Tris buffered saline) on ice for 1 hr, the lysate thus obtained was transferred to nitrocellulose paper and analyzed for EGFR phosphorylation by Western blotting using a phospho-EGFR antibody (Cell Signal).

As shown in FIGS. 3A and 3B, the activity of EGFR increased with an increase of EGF concentration to up to 16 nM, peaking at the time point of 5 min.

For screening about 50 ERBB2-binding aptamers, accordingly, EGF-induced tyrosine phosphorylation of EGFR was measured after treatment with 10 nM EGF for 5 min in the presence of the aptamers.

Figure 4A:
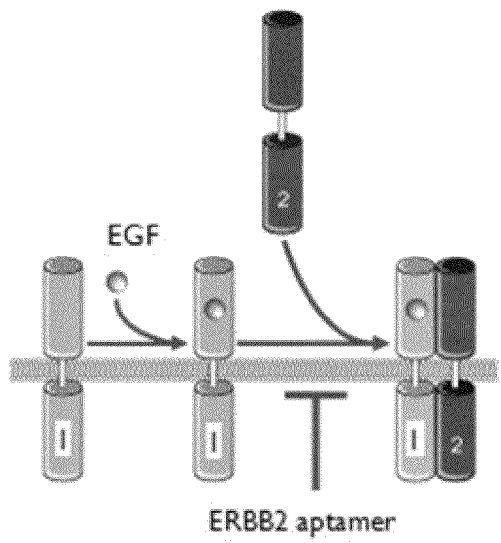
FIG. 4A is a schematic view illustrating a screening procedure for ERBB2 inhibition using the ERBB2 aptamer (1: EGFR, 2: ERBB2 aptamer)

A431 cells (ATCC) were immobilized on 6-well plates, and starved for 24 hrs in serum-free DMEM (HyClone) before incubation in the co-presence of 10 nM EGF (P01133, Sigma) and each aptamer in DMEM for 5 min. Afterwards, the medium was removed, and the cells were treated with 300 µL of a lysis buffer (1% Triton X-100, Tris buffered saline) and harvested with a scrapper. They were incubated for 1 hr on ice, and centrifuged at 4° C. at 1000 g for 10 min. Only the supernatant was taken, run on agarose by electrophoresis, and transferred to nitrocellulose paper. Western blotting with an anti-human phospho ERBB2 antibody (Cell Signal) determined the phosphorylation of ERBB2. This screening procedure is schematically illustrated in FIG. 4A. It was designed to examine the inhibitory activity of the ERBB2 aptamers against the hetero-dimerization of EGFR and ERBB2.

Figure 4B:
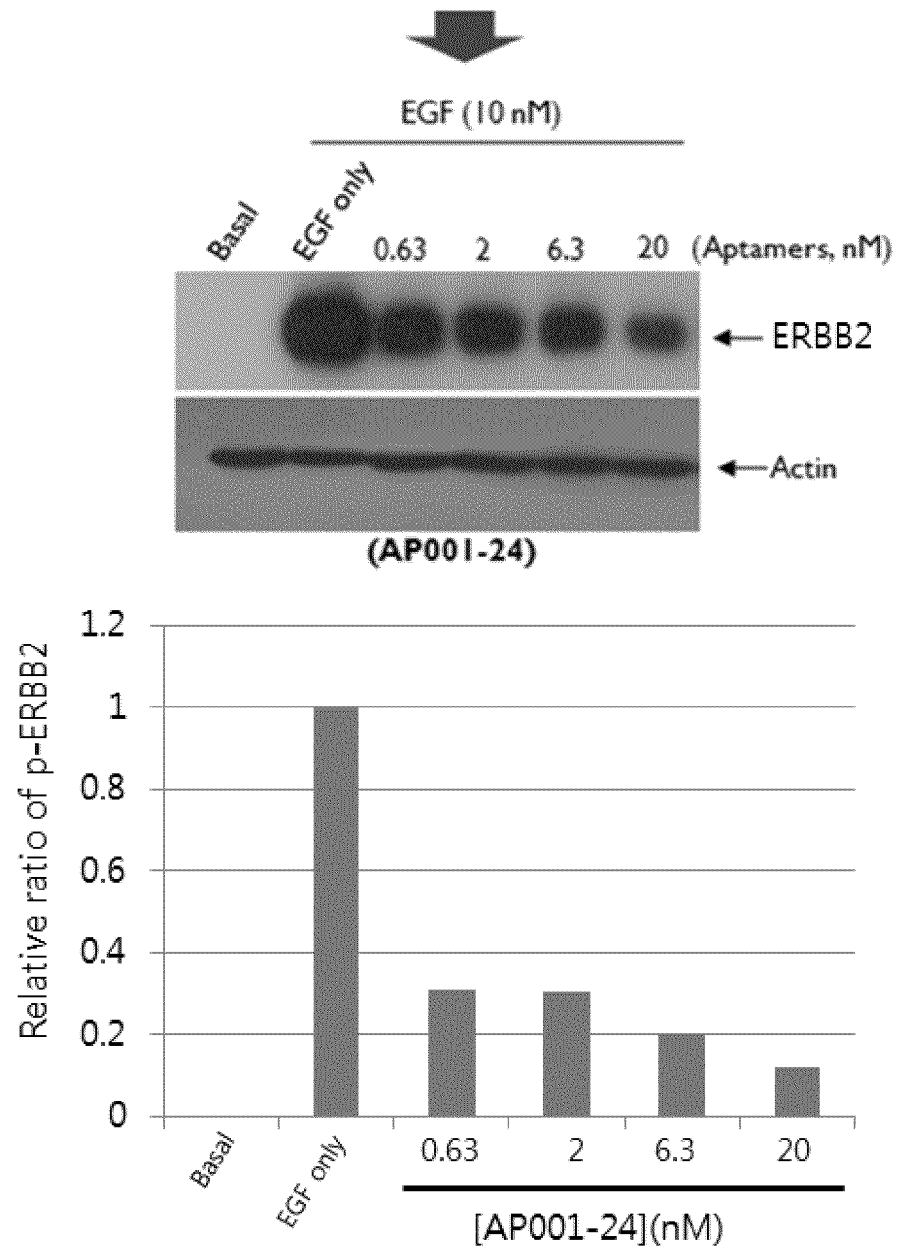
FIG. 4B shows the screening results obtained by use of AP001-24 (SEQ ID NO: 11).

Fifty aptamers listed in Table 2 were measured for p-ERBB2 inhibition according to aptamer concentration (0.63, 2, 6.3, 20 nM). As a result, AP001-24 (SEQ ID NO: 11) was observed to be the most inhibitory of EGF-induced ERBB2 activation (phosphorylation). The results are shown in FIG. 4B. AP001-24 exhibited an $IC_{50}$ of about 1 nM with regard to ERBB2.

2.2: Anti-Cancer Effect of ERBB2 Aptamer

The ERBB2 aptamers were observed for ability to block EGF- or HRG-mediated EGFR-ERBB2 or ERBB2-ERBB3 hetero-dimerization and its cancer survival-related downstream signaling pathway mediated by AKT and ERK.

Figure 5A:
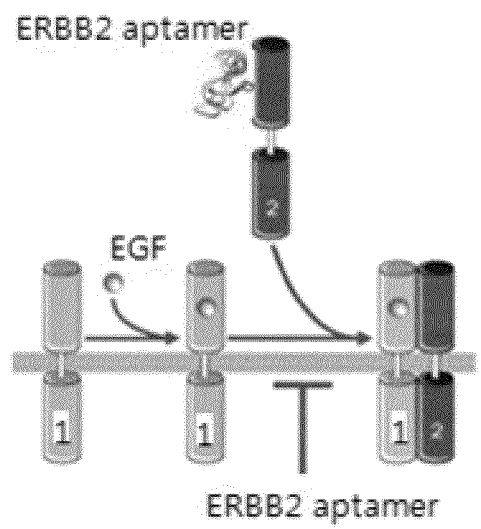
FIGS. 5A and 5B are schematic views illustrating the inhibitory activity of the ERBB2 aptamer (green) against ERBB2 activity (Tyr877 phosphorylation) by blocking EGF- or HRG-mediated dimerization, respectively.
Figure 5B:
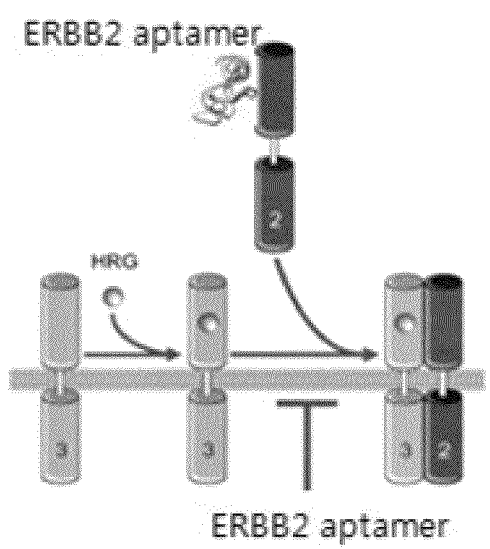

FIGS. 5A and 5B are schematic views illustrating the inhibitory activity of each ERBB2 aptamer (green) against ERBB2 activity (Tyr877 phosphorylation) by blocking EGF- or HRG-mediated dimerization.

Figure 5C:
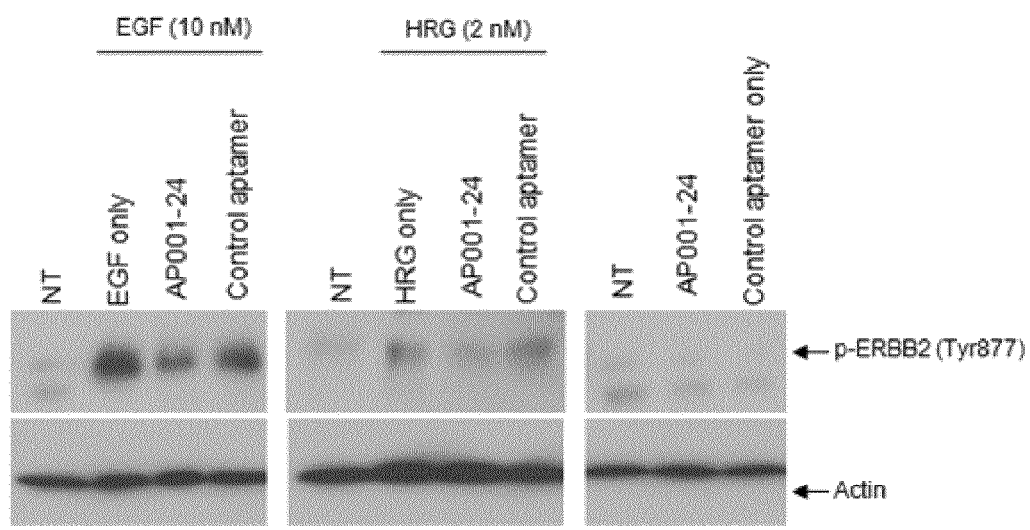
FIG. 5C shows data indicating the inhibitory activity of the ERBB2 aptamer (green) against ERBB2 activity (Tyr877 phosphorylation) by blocking EGF- or HRG-mediated dimerization (NT: No Treatment, Control aptamer: Ap001-24 의 reverse complement sequence).

While EGF or HRG induced or mediated ERBB2 activation (Tyr877), the activation was observed to be blocked in the presence of the ERBB2 aptamer AP001-24 (SEQ ID NO: 11). In this regard, the A431 cell line (ATCC) was immobilized on 6-well plates, and cultured to 50%-70% confluence. At this time, the medium was changed with DMEM (HyClone) devoid of growth factors. After 24 hours of serum starvation, the cells were incubated for 15 min with the aptamer in a final concentration of 20 nM, and then for an additional 5 min in the presence of 10 nM EGF (P01133, Sigma), or 2 nM HRG (Q02297, Sigma). Subsequently, the supernatant was discarded, and the cells were treated for 1 hr with 300 µL of a lysis buffer (1% Triton X-100, Tris buffered saline) on ice. The cell lysates thus obtained was centrifuged for 5 min at 4° C. at 15000 rpm (table top centrifuge, Eppendorf). The resulting supernatant was electrophoresed, transferred to nitrocellulose paper, and subjected to Western blotting using a phospho-ERBB2 specific antibody (Cell Signal) (FIG. 5C, NT: No Treatment, Control aptamer: reverse complement sequence of Ap001-24).

Also, the inhibition of AP001-24 aptamer against ERBB2 activation was observed to lead to blocking the ERBB2 downstream signaling mediated by Akt and ERK, which plays an important role in the growth of cancer cells.

Figure 6:
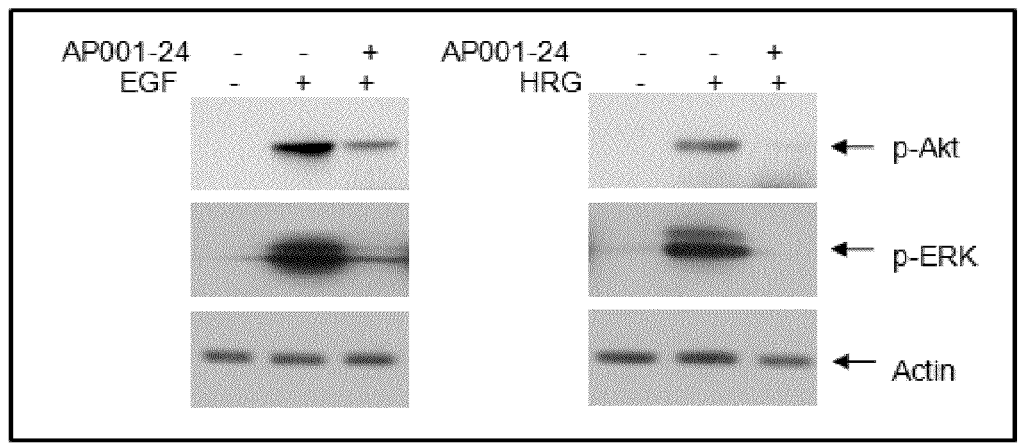
FIG. 6 shows Western blots illustrating the inhibitory activity of the ERBB2 aptamer AP001-24 (SEQ ID NO: 11) against AKt and ERK

In this respect, the A431 cell line (ATCC) was immobilized on 6-well plates, and cultured to 50%-70% confluence. At this time, the medium was changed to DMEM (HyClone) devoid of growth factors. After 24 hours of serum starvation, the cells were incubated for 15 min with the aptamer in a final concentration of 20 nM, and then for an additional 5 min in the presence of 10 nM EGF (P01133, Sigma), or 2 nM HRG (Q02297, Sigma). Subsequently, the supernatant was discarded, and the cells were treated for 1 hr with 300 µL of a lysis buffer (1% Triton X-100, Tris buffered saline) on ice. The cell lysate thus obtained was centrifuged for 5 min at 4° C. at 15000 rpm (table top centrifuge, Eppendorf). The resulting supernatant was electrophoresed, transferred to nitrocellulose paper, and subjected to Western blotting using a phospho-Akt specific antibody (Cell Signal) and a phospho-ERK specific antibody (Cell Signal) (FIG. 6).

2.3: Specificity of ERBB2 Aptamer

To examine whether the excavated ERBB2 aptamer specifically binds to ERBB2 alone, binding affinities of the ERBB2 aptamer AP001-24 (SEQ ID NO: 11) for ERBB2 and EGFR (Acc# P04412), which are similar in amino acid sequence, were compared therebetween.

For this, the aptamer was terminally labeled with α-$P^{32}$ ATP (Perkin Elmer) and TdT (Terminal deoxynucleotidyl transferase, NEB). The library DNA 1 μM, obtained through the SELEX procedure, 0.25 μL α-$P^{32}$ ATP (5 μM, Perkin Elmer), 0.25 μL TdT, and a reaction volume of 10 μL of 10×NEB buffer4 (NEB) were reacted at 37° C. for 30 min, followed by incubation at 70° C. for 10 min to inactivate TdT. The labeled DNA pool was filtered using Micro spin G-50 column (GE healthcare).

Figure 7A:
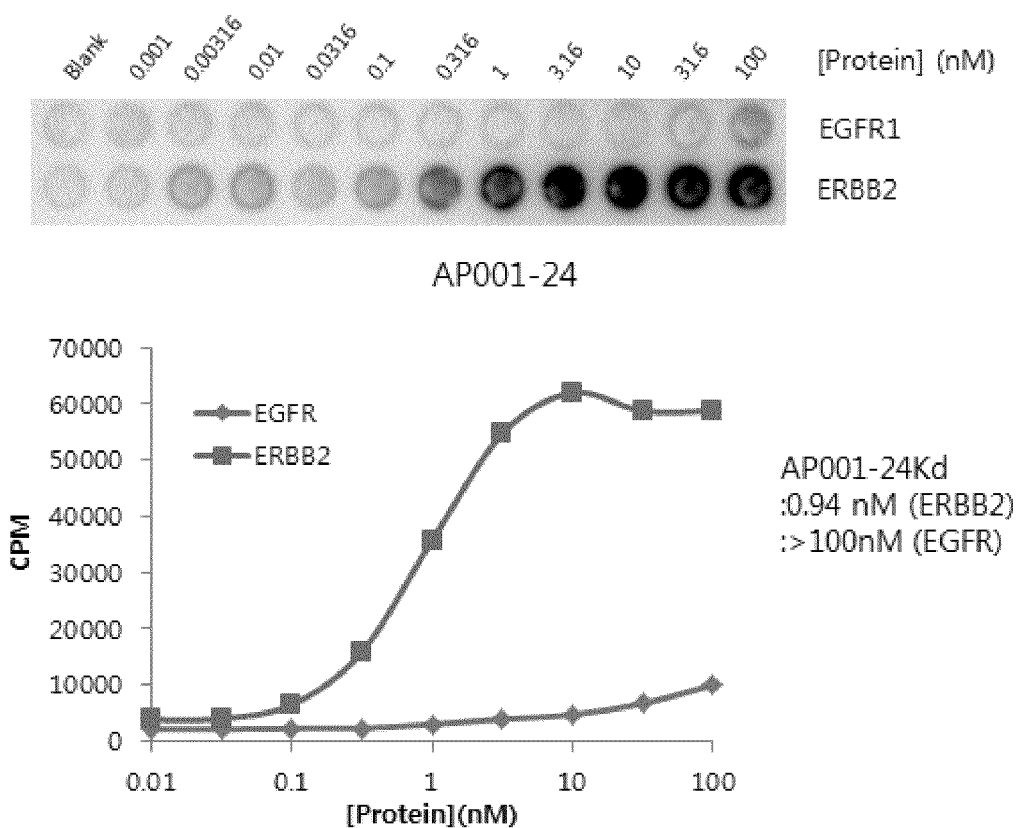
FIG. 7A shows results of an assay for the binding affinity of the ERBB2 aptamer AP001-24 (SEQ ID NO: 11) for EGFR and ERBB2 (X-axis: concentration of target protein (nM), Y-axis: cpm).

The labeled DNA pool was added at a dose of 20,000 cpm to 100 μL of 1×SB buffer (200 mM HEPES, 510 mM NaCl, 25 mM KCl, 25 mM $MgCl_2$), and cooled slowly from 95° C. to 37° C. at a decreasing rate of 0.1° C. per second. A 12-point serial dilution of the ERBB2 protein (R&D systems, 1129-ER-050) was conducted from 100 nM in a buffer (200 mM HEPES, 510 mM NaCl, 25 mM KCl, 25 mM $MgCl_2$), and reacted with 30 μL of each of the heated and cooled DNA pools at 37° C. for 30 min. A nylon membrane (GE healthcare) was spotted with 2 μL of each DNA-ERBB2 mixture and then added with 5.5 μL of Zorbax resin (Agilent). It was added to a Durapore filter (Millipore) which was previously wetted with 50 μL of 1×SB buffer (200 mM HEPES, 510 mM NaCl, 25 mM KCl, 25 mM $MgCl_2$), followed by producing a vacuum. Then, the membrane filter was rinsed with 100 μL of 1× selection buffer (200 mM HEPES, 510 mM NaCl, 25 mM KCl, 25 mM $MgCl_2$). The filter plates were exposed overnight to image plates, and the images thus formed on the image plates were quantitatively analyzed using FLA-5100 (Fuji). The results are shown in FIG. 7A. As can be seen in FIG. 7A, the binding affinity of the aptamer of the present invention was measured to be at least 1,000-fold higher for ERBB2 than for the EGFR receptor.

Figure 7B:
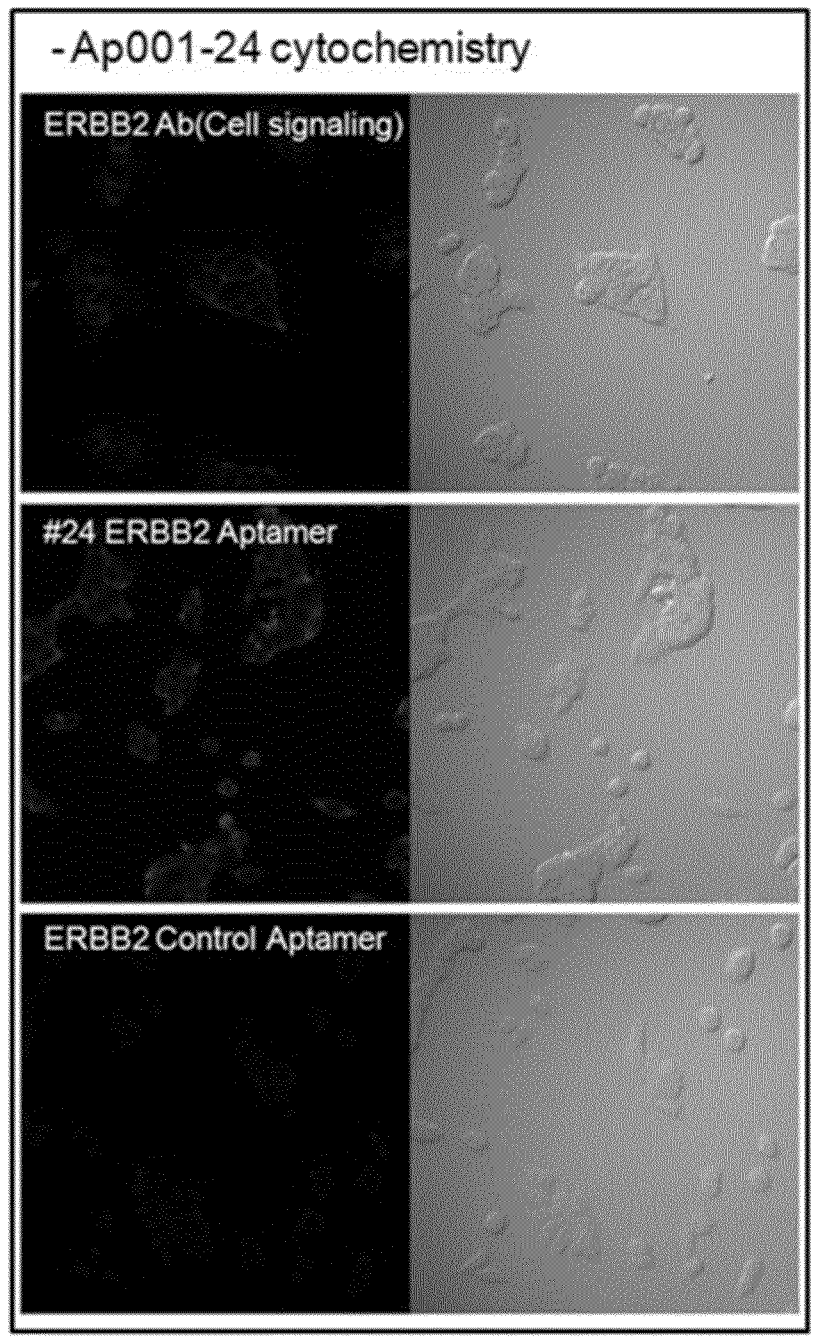
FIG. 7B shows cytochemical results indicating the binding affinity of the ERBB2 aptamer AP001-24 (SEQ ID NO: 11) with ERBB2 in MCF7.
Figure 7C:
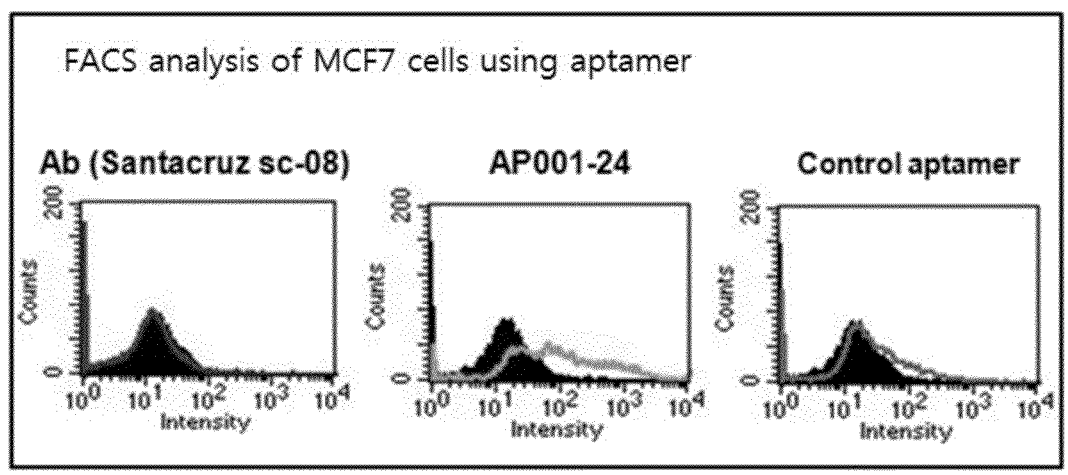
FIG. 7C shows results of the FACS assay (Control aptamer: Reverse complement sequence of Ap001-24).

In addition, the ERBB2 aptamer AP001-24 (SEQ ID NO: 11) was conjugated with a Cy3 fluorescent (BioGenex), and applied to the analysis of binding to ERBB2 in the breast cancer cell line MCF7 (ATCC) through cytochemistry (FIG. 7B), and FACS assay (FIG. 7C).

For cytochemistry, MCF7 cells (ATCC) were cultured in 24-well plates with cover glass. When they became 30-50% confluent, the cells were fixed with PBS containing 1% (w/v) para-formaldehyde, and then blocked for 15 min with Tris-buffered saline containing 1% BSA. Thereafter, the cells were treated with an ErBB2 specific antibody (Cell Signaling) which was previously 1:1000 (v/v) diluted in PBS containing 1% (w/v) BSA (RnD Systems). Alternatively, the cells were treated with 10 pmole of the aptamer AP001-24 (SEQ ID NO: 11) at 37° C. for 30 min Subsequently, the cover glass was washed three times with PBS, dehydrated and dried, and mounted on permount-coated slide glass, followed by microscopy.

For use in an FACS assay, MCF7 cells (ATCC) were grown to a population of 5×$10^4$~2×$10^5$ cells in a 10-cm plate, detached with 2 mM EDTA, and washed with PBS of 4° C. Thereafter, they were treated with an antibody or an aptamer. In the case of antibody, the cells were treated at 4° C. for 60 min which an ErBB2 specific antibody (Santa Cruz) which was previously diluted 1:1000 (v/v) in PBS containing 1% (w/v) BSA (RnD Systems). Then, the cells were washed three times with PBS, and treated with an FITC-conjugated secondary antibody (Santa Cruz) at RT for 30 min. As for the aptamer, the cells were incubated at 4° C. for 1 hr with 100 pmoles of the aptamer AP001-24 (SEQ ID NO: 11), and washed with PBS of 4° C. After treatment with the antibody or the aptamer, the cells were fixed with 1.5 ml of a 1% (w/v) paraformaldehyde solution at 4° C., and measured by FACS (FACS Calibur flow cytochemistry, BD Bioscience).

As is apparent from data of FIGS. 7B and 7C, the ERBB2 aptamer AP001-24 (SEQ ID NO: 11) was found to bind specifically to ERBB2 only (control aptamer: reverse complement sequence of Ap001-24).

Example 3

Preparation of ERBB2 Aptamer Agents

From Truncated aptamer AP001-24 (SEQ ID NO: 11), four different ERBB2 aptamer formulations were synthesized, as follows.

E1: (2'-OMeU)$_2$-ERBB2 aptamer-(2'-OMeU)$_2$(2'-OMeU)$_2$-Cy3-O-(AP001-24)-O-(2'-OMeU)$_2$-T]

E2: PEG-ERBB2 aptamer-idT [Cy3-T-$PEG_{784}$-O-(AP001-24)-idT]

E3: ERBB2 aptamer-idT [Cy3-O-(AP001-24)-idT]

E4: ERBB2 aptamer [Cy3-O-(AP001-24)-OH]

(T: 2'-deoxyThymidine (Thymidine), idT: inverted deoxythymidine)

(Molecular weight of PEG: 784 Da)

After purification, the aptamer agents were dissolved in secondary distilled water to give 0.1 mM aptamer solutions.

The ERBB2-aptamer agents were examined for stability in blood by measuring their serum half lives. Briefly, the aptamer agents were left at 94° C. for 4 min, and slowly cooled to room temperature over 1 hr so as to form their exact secondary structures. Forty μL (4 nmoles) of each of the aptamer solutions was vigorously mixed with 200 μL of human serum (Human male AB) by vortexing, and the mixture was aliquoted in an amount of 20 μL per tube into 10 E-tubes and incubated in a 37° C. incubator. Each sample was taken after 10 min, 30 min, 1 h, 2 h, 4 h, 8 h, 21 h, 24 h, 30 h, 48 h, and 72 h of incubation, and stored in a deep freezer until analysis. Immediately before analysis, each sample was added with 20 μL of distilled water, and 10 μL was withdrawn from each dilution and quantitatively analyzed by Anion Exchange HPLC (Column: GE Healthcare, HPLC: Waters). The HPLC data indicative of the amounts of the aptamer in serum were graphically depicted to determine the stability of the ERBB2 aptamers in serum.

For the HPLC, an Anion exchange Resource-Q column was used, together with 25 mM Tris-HCl pH 8.5 as A buffer, and 1 M NaCl 25 mM Tris-HCl pH 8.5 as B buffer. The amount of B buffer was increased from 10% (v/v) to 100% (v/v) over 25 min. Fluorescence was measured at 566 nm after a wavelength of 551 nm was irradiated.

Results of the analysis are summarized in Table 6, below.

TABLE 6

| | 10 min | 30 min | 1 h | 4 h | 8 h | 21 h | 24 h | 30 h | 48 h | 72 h |
|---|---|---|---|---|---|---|---|---|---|---|
| (2'-OMeU)2-Cy3-1194-34-O-(2'-OMeU)2-T | 100.0 | 99.4 | 98.6 | 98.6 | 93.9 | 94.0 | 93.1 | 90.3 | 87.0 | 82.2 |
| Cy3-T-PEG784-1194-34-idT | 100.0 | 94.9 | 94.7 | 94.4 | 94.2 | 93.9 | 92.7 | 88.6 | 88.4 | 83.9 |
| Cy3-1194-34-idT | 100.0 | 98.8 | 96.3 | 96.6 | 97.0 | 94.7 | 93.5 | 90.3 | 87.3 | 77.0 |
| Cy3-1194-34-idT | 100.0 | 97.7 | 97.7 | 95.0 | 89.9 | 88.0 | 83.7 | 78.9 | 70.4 | 66.0 |

It is apparent from the data that three of the four ERBB2 aptamers are stable in serum as they have a half life in serum of more than 72 hrs or longer ($t_{1/2}$ in serum>72 hr). Particularly, modification at both 5' and 3' termini significantly increased the serum stability of the aptamers.

Based on the data, the aptamer agents are stable in serum in the following order:

PEG-ERBB2 aptamer-idT (E2)=(2'-OMeU)$_2$-ERBB2 aptamer-(2'-OMeU)$_2$ (E1)>ERBB2 aptamer-idT (E3)>ERBB2 aptamer (E4)

Figure 8:
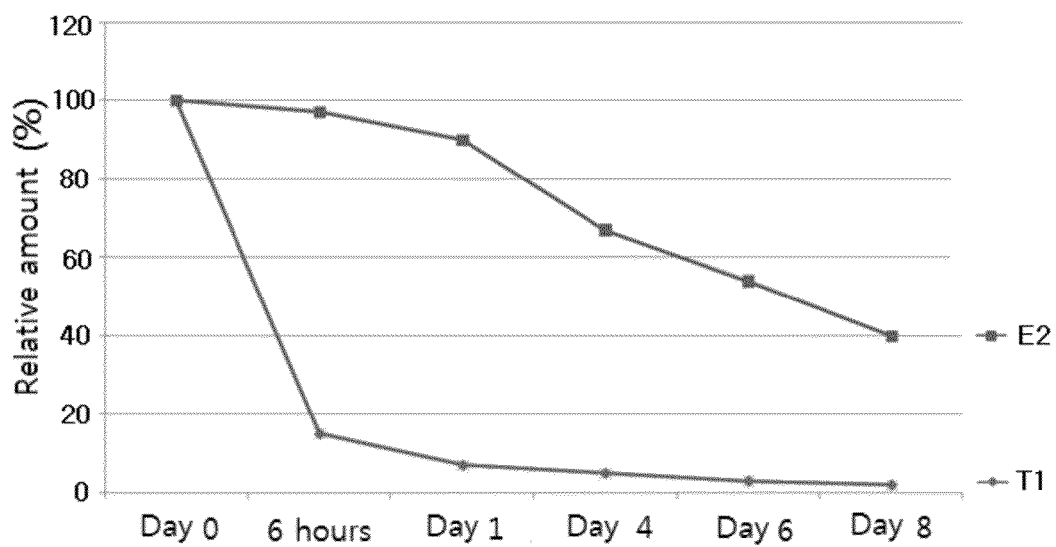
FIG. 8 shows a comparison the half life in serum of PEG-ERBB2 aptamer-idT (E2), prepared in Example 3, with that of the control T 40-mer aptamer (T1).

The half life in serum of the most stable PEG-ERBB2 aptamer-idT (E2) was compared to that of the control T 40-mer aptamer (T1, 40 repeats of T). Half-life measurements obtained in the same manner as above mentioned are given in FIG. 8 (???). As can be seen in FIG. 8(???), the half-life in serum was measured to be 3 hrs for T1 ($t_{1/2}$ in serum=3 hr) and 170 hrs for PEG-ERBB2 aptamer-idT (E2) ($t_{1/2}$ in serum=170 hr), demonstrating that the modified ERBB2 aptamers of the present invention are very stable in serum.

Example 4

In Vito Efficacy of ERBB2 Aptamer Agent (PEG-ERBB2 Aptamer-idT)

Experimental Procedure
Establishment of Animal Model:
Balb/c nude female mice 6 weeks after birth were established to in vivo tumor models. The mice weighed 20 g on average. An estradiol pellet was subcutaneously implanted to the back of each mouse. The human breast cancer cell line BT-474 was purchased from the ATCC, and grown. Two days after pellet implantation, the BT-474 cells were subcutaneously injected in an amount of $5 \times 10^7$ cells to thigh of the mice to allow for tumor formation. Thereafter, the mice were monitored every day for tumor growth with the naked eye, and the tumor size was measured using a caliper.

FDG PET Image:
FDG PET was performed on the mice to certify oncogenesis. The mice were given no food, except for water 24 hrs before tomography. F-18 FDG (F-18 fluorodeoxyglycose, the Cyclotron Center of the Department of Nuclear Medicine, the Severance Hospital, Seoul) was intraperitoneally injected at a dose of 220-230 μCi to the mice, and one hour later, images were obtained by Siemens Inveon animal PET (Positron emission tomography). The aptamers were applied, and FDG PET imaging was again conducted according to the same protocol so as to determine therapeutic effects.

ERBB2 Aptamer Therapy:
The ERBB2 aptamer (AP001-24, SEQ ID No: 11) and the ERBB2 aptamer agent (E2 agent, PEG-ERBB2 aptamer-idT, AP001-24, SEQ ID No: 11) were intraperitoneally injected at respective doses of 5 mg/kg and 20 mg/kg into the mice every day for 5 days. For a control, intraperitoneal injections were conducted with 200 ul of PBS. Tumor sizes were measured every two or three days using a caliper, and FDG PET images were taken on day 6.

Figure 9:
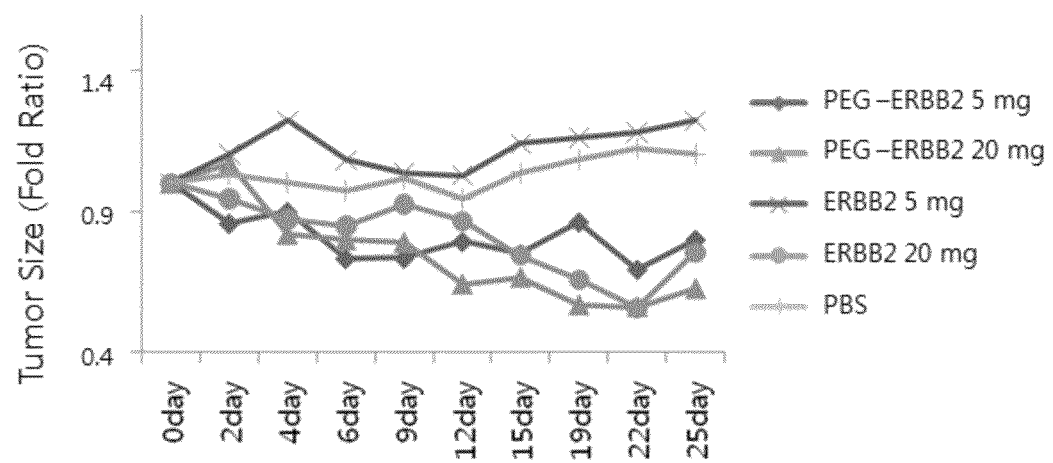
FIG. 9 is a graph in which sizes of breast cancer tissues in mice are plotted as a function of time after the administration of ERBB2 aptamers.

Results
Change in Tumor Size:
Tumor sizes were measured in mice administered with the ERBB2 aptamer agent (PEG-ERBB2, E2), and compared with those measured when administered with PBS. Results are given in FIG. 9. As can be seen in FIG. 9, significant changes in tumor size were detected upon administration with 5 mg or 20 mg of ERBB2 aptamer agent (PEG-ERBB2, E2) or with 20 mg of ERBB2. Going beyond 7 days after the termination of the regimen, the reductive effect on tumor size was continued for more than two weeks.

Figure 10:
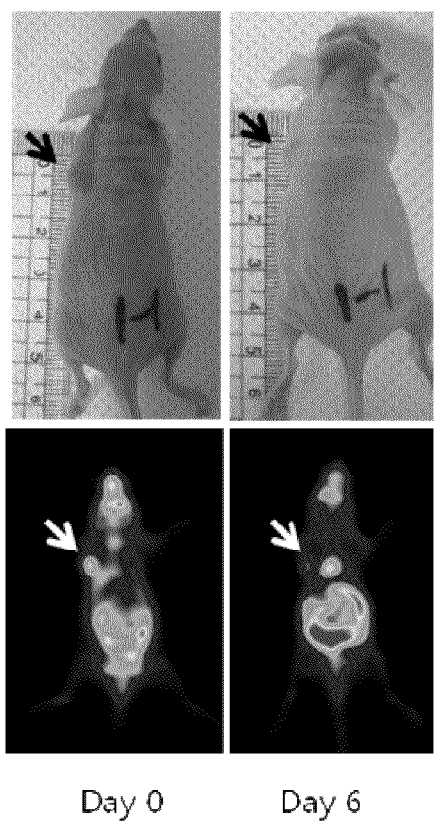
FIG. 10 shows photographic findings (upper panel) and FDG PET images (lower panels) before (Day 0) and after treatment (Day 6) with the ERBB2 aptamer.

FDG PET Imaging:
Tumor metabolism was assessed using FDG PET images, and the results are given in FIG. 10. As can be seen in FIG. 10, the tumor glucose metabolism which was observed to be highly active before the treatment was lowered on day 6 after the ERBB2 aptamer (PEG-ERBB2, E2) was intraperitoneally injected at a dose of 5 mg/kg, as analyzed by FDG PET, demonstrating that the ERBB2 aptamer agent restrained tumor glucose metabolism. In addition, tumor sizes (arrows???) were reduced.

In the tumor mouse models, the ERBB2 aptamer agent was found to significantly reduce tumor size compared to the control. Further, FDG PET, which can monitor tumor glucose metabolism, exhibited a significant reduction in tumor glucose metabolism after treatment with the ERBB2 aptamer. The data obtained from tumor size monitoring and glucose metabolism assessment indicated that the ERBB2 aptamer agent has an anti-cancer effect on the breast cancer cell line BT-474.

Example 5

Assay for In Vivo Stability of Aptamer Agent 5.1. Toxicity in ICR Mice Intravenously Injected with the Aptamer Agent An assay was carried out to approximate the toxicity induced by single intravenous injection of the aptamer agent to ICR mice. The aptamer agent PEG-ERBB2 aptamer-idT, having 40 kDa PEG, was used as a test material.

Single injections of the test material were given at a dose of 0 (vehicle control), 10, 100, and 1,000 mg/kg to 10 mice per group (5 males and 5 females in each group), and mortality, general symptoms, weights, and necropsy findings were examined, and compared with those obtained in the vehicle control.

Material and Method
As a test material, the 40 kDa PEG-ERBB2 aptamer-idT (E2) prepared from ERBB2 aptamer (AP001-24) and PEG in Example 3 was used. 1×D-PBS (Dulbecco's Phosphate-Buffered Saline, GIBCO) was selected as a vehicle not only because it can well dissolve the test material but also because it was accepted in toxicity tests upon intravenous injection. Specific pathogen-free (SPF) mice, such as HsdKoat:ICR (CD-1® Koatech), which were 7 weeks old were purchased. They counted 24 of each sex, with a mean weight of 30.13-32.97 g for males, and 23.81-26.36 g for females. Upon administration, they were 8 weeks old, and counted 20 each gender, with a mean weight of 31.33-34.70 g for males and 24.87-27.40 g for females.

Referring to the examination test report on pathogens from the animal provider, the purchased animals went into quarantine. After arrival, the animals were acclimated to the test environment for 5 days during which healthy animals were selected by observing general symptoms.

The animals had been bred in Room 3 of the 2$^{nd}$ Animal Breeding Area in the Pre-Clinical Research Center of Chemon Inc., which was kept at a temperature of 23±3° C. and a relative humidity of 55±15%, under lighting for 12 hrs (light on 8 A.M., light off 8 P.M.) at an intensity of 150-300 Lux, with 10-20 ventilation rounds/hr. All testers wore autoclaved (121° C., 20 min) working clothes and protection equipment before performing experiments. @ @ @ @ During experiments, the animal lab was kept at a temperature of 22.5-22.8° C. and a relative humidity of 63.7-69.2% under an automatic control system. Other environment factors such as the number of ventilation, illumination intensity, etc., were regularly measured according to the standard operating procedures (SOPs) of the Pre-Clinical Research Center, Chemon, Inc. Any deviation that might affect test results was not detected at all. The animals were lodged in stainless steel wire cages (W 165×L 240×H 145 mm) at a density of one male/cage during the entire period of experiment, and at a density of five females/cage for the period of quarantine and acclimation and at a density of three/cage during the period of administration and observation. As the feedstuff for the experiment, radio-sterilized solid diets were provided from Koatech (Teklad Certified Irradiated Global 18% Protein Rodent Diet, 2918C, Harlan Co. Ltd., USA), and the animals were allowed to have access to the diet ad libitum. No factors that might have influences on test results were found in the examination report of ingredient analysis.

Water was freely provided as being contained in a bottle after underground water was allowed to undergo UV sterilization and ultra-filtration. The water passed the criteria for drinking water, as analyzed in the Gyeonggi Institute of Hygiene and Environment (324-1, Pajang-dong, Jangan-gu, Suwon, Gyeonggi, Korea).

This experiment was approved by the Institutional Animal Care and Use Committee of the Pre-Clinical Research Center, Chemon, Inc., pursuant to the Animal Protection Law (legislated as law 4379 on May 31, 1991, partially revised to law 8852 on Jan. 29, 2008).

Test Group and Dose
Test groups were organized as follows:

TABLE 7

| Group | Gender | Population | Animal No. | Amount of Administered Solution (mL/kg) | Dose (mg/kg) |
|---|---|---|---|---|---|
| G1[a] | M/F | 5/5 | 01-05/21-25 | 10 | 0 |
| G2 | M/F | 5/5 | 06-10/26-30 | 10 | 10 |
| G3 | M/F | 5/5 | 11-15/31-35 | 10 | 100 |
| G4 | M/F | 5/5 | 16-20/36-40 | 10 | 1,000 |

[a]vehicle control group (1X D-PBS)

As for the dose, its maximum was given 1,000 mg/kg, with two values descendent at a common ratio of 10 from the maximum value. Also, 1×D-PBS alone was administered for a vehicle control.

The animals were divided into groups as follows. The animals which were determined as being healthy during the period of acclimation were weighed, and selection was made of 20 mice for each gender the weights of which were proximate to the mean value. They were ranked in terms of weight, and random combinations of them were established according to the group set forth in the 'organization of test groups' so that their weights were distributed over the groups as uniformly as possible. After grouping, the excess animals were used as exercises.

Individual identification was achieved using oil-based ink marks on the skin during the period of acclimation, and using saturated picric acid solution on the skin during the period of administration and observation. Identity cards of different colors were issued the breeding cages to discriminate the different doses administered to the animals, with identification numbers designated for cage dies. An information card describing experiment number, the period of use of animal room, the name of staff responsible for the experiment, the name of experimenter, the network of emergency contacts, etc. was attached on the entrance door of the breeding room.

The test materials were used without adjusting purity, and formulated just before administration. For use in the high-dose group, the test materials were weighed and dissolved at a concentration of 100 mg/mL in a vehicle. For the medium- and low-dose groups, the formulation of the high-dose group was serially diluted in the same vehicle. The formulation of the high-dose group was observed to have a pH of 6.0-6.5, as measured by pH Test Strip (P-4536, SIGMA).

An intravenous injection was conducted since it would be a clinical route for human. After each animal was confined into a restrainer, the tail was rubbed with 70% alcohol cotton, and the alcohol was wiped off with gauze. Using a 26 G syringe, the formulations were injected at a rate of 1 mL/min into the tail vein. The formulations amounted to 10 mL/kg based on the weight measured on the day of administration after starvation. A single injection was conducted once a day and completed before 11:30 A.M. The day of administration was designated as day 0.

Observation and Examination Item

For general symptoms and death, the animals were monitored continuously until 1 hr from the injection and then, every hour from 1 to 6 hrs after injection. Then, observation was made one or more times every day until 14 days after injection.

All the animals were weighed prior to injection and day 1, 3, 7 and 14, and the weights of dead animals were obtained as soon as they had been found.

Day 14, laparotomy was performed on all living animals after anesthetization with $CO_2$, and the post-caval vein and the saphenous vein were cut to release blood to exanguination. For autopsy findings, then, the body surface and internal organs were scrutinized with the naked eye.

Statistical significance of the weight and weight gain data was evaluated using one-way ANOVA, and values of $P<0.05$ were considered as significant. The assumption of normality satisfied homoscedasticity, as assayed by Levene's test, and thus Duncan's multiple range test was conducted. Median lethal doses ($LD_{50}$) for dead animals were assessed according to Probit analysis, and computer software for statistics was SPSS 10.1 K.

Results
Results obtained above are summarized in Tables 8 to 17, below.

TABLE 8

Results of toxicity tests when the aptamer agent (E2) is intravenously administered once into an ICR mouse

STUDY: 10-MA-337

| groups (mg/kg) | No. DEAD/ No. DOSED | DAYS AFTER DOSE | | | | | | | | | SEX: MALE $LD_{50}$[a] Value |
|---|---|---|---|---|---|---|---|---|---|---|---|
| | | 0 | 1 | 2 | 3 | 4 | 5 | 6 | 7 | 8-14 | |
| G1 (0) | 0/5 | 0 | 0 | 0 | 0 | 0 | 0 | 0 | 0 | 0 | |
| G2 (10) | 0/5 | 0 | 0 | 0 | 0 | 0 | 0 | 0 | 0 | 0 | |

TABLE 8-continued

Results of toxicity tests when the aptamer agent (E2) is intravenously administered once into an ICR mouse

STUDY: 10-MA-337

| groups (mg/kg) | No. DEAD/ No. DOSED | DAYS AFTER DOSE | | | | | | | | |
|---|---|---|---|---|---|---|---|---|---|---|
| | | 0 | 1 | 2 | 3 | 4 | 5 | 6 | 7 | 8-14 |
| G3 (100) | 0/5 | 0 | 0 | 0 | 0 | 0 | 0 | 0 | 0 | 0 |
| G4 (1,000) | 1/5 | 0 | 0 | 0 | 0 | 0 | 0 | 0 | 1 | 0 | 1215.8 mg/kg |

SEX: FEMALE
ALD[b] Value

| G1 (0) | 0/5 | 0 | 0 | 0 | 0 | 0 | 0 | 0 | 0 | 0 |
| G2 (10) | 0/5 | 0 | 0 | 0 | 0 | 0 | 0 | 0 | 0 | 0 |
| G3 (100) | 0/5 | 0 | 0 | 0 | 0 | 0 | 0 | 0 | 0 | 0 |
| G4 (1,000) | 0/5 | 0 | 0 | 0 | 0 | 0 | 0 | 0 | 0 | 0 | >1,000 mg/kg |

[a]$LD_{50}$: Lethal Dose 50
[b]ALD: Approximate Lethal Dose

TABLE 9

Clinical Findings in Male Mice

STUDY: 10-MA-337  CLINICAL SIGNS  Sex: MALE

| groups (mg/kg) | Animal ID | SIGNS | OBSERVED ON[a] |
|---|---|---|---|
| G1 (0) | 1 | Normal | DAY 0-14 |
| | | Terminal sacrifice | DAY 14 |
| | 2 | Normal | DAY 0-14 |
| | | Terminal sacrifice | DAY 14 |
| | 3 | Normal | DAY 0-14 |
| | | Terminal sacrifice | DAY 14 |
| | 4 | Normal | DAY 0-14 |
| | | Terminal sacrifice | DAY 14 |
| | 5 | Normal | DAY 0-14 |
| | | Terminal sacrifice | DAY 14 |
| G2 (10) | 6 | Normal | DAY 0-14 |
| | | Terminal sacrifice | DAY 14 |
| | 7 | Normal | DAY 0-14 |
| | | Terminal sacrifice | DAY 14 |
| | 8 | Normal | DAY 0-14 |
| | | Terminal sacrifice | DAY 14 |
| | 9 | Normal | DAY 0-14 |
| | | Terminal sacrifice | DAY 14 |
| | 10 | Normal | DAY 0-14 |
| | | Terminal sacrifice | DAY 14 |
| G3 (100) | 11 | Normal | DAY 0-14 |
| | | Terminal sacrifice | DAY 14 |
| | 12 | Normal | DAY 0-14 |
| | | Terminal sacrifice | DAY 14 |
| | 13 | Normal | DAY 0-14 |
| | | Terminal sacrifice | DAY 14 |
| | 14 | Normal | DAY 0-14 |
| | | Terminal sacrifice | DAY 14 |
| | 15 | Normal | DAY 0-14 |
| | | Terminal sacrifice | DAY 14 |
| G4 (1,000) | 16 | Normal | DAY 0-14 |
| | | Terminal sacrifice | DAY 14 |
| | 17 | Normal | DAY 0-14 |
| | | Terminal sacrifice | DAY 14 |
| | 18 | Normal | DAY 0-6 |
| | | Death | DAY 7 |
| | 19 | Normal | DAY 0-14 |
| | | Terminal sacrifice | DAY 14 |
| | 20 | Normal | DAY 0-14 |
| | | Terminal sacrifice | DAY 14 |

[a]The day of administration was designated as day 0.

TABLE 10

Clinical Findings in Female Mice

STUDY: 10-MA-337  CLINICAL SIGNS  Sex: FEMALE

| groups (mg/kg) | Animal ID | SIGNS | OBSERVED ON[a] |
|---|---|---|---|
| G1 (0) | 21 | Normal | DAY 0-14 |
| | | Terminal sacrifice | DAY 14 |
| | 22 | Normal | DAY 0-14 |
| | | Terminal sacrifice | DAY 14 |
| | 23 | Normal | DAY 0-14 |
| | | Terminal sacrifice | DAY 14 |
| | 24 | Normal | DAY 0-14 |
| | | Terminal sacrifice | DAY 14 |
| | 25 | Normal | DAY 0-14 |
| | | Terminal sacrifice | DAY 14 |
| G2 (10) | 26 | Normal | DAY 0-14 |
| | | Terminal sacrifice | DAY 14 |
| | 27 | Normal | DAY 0-14 |
| | | Terminal sacrifice | DAY 14 |
| | 28 | Normal | DAY 0-14 |
| | | Terminal sacrifice | DAY 14 |
| | 29 | Normal | DAY 0-14 |
| | | Terminal sacrifice | DAY 14 |
| | 30 | Normal | DAY 0-14 |
| | | Terminal sacrifice | DAY 14 |
| G3 (100) | 31 | Normal | DAY 0-14 |
| | | Terminal sacrifice | DAY 14 |
| | 32 | Normal | DAY 0-14 |
| | | Terminal sacrifice | DAY 14 |
| | 33 | Normal | DAY 0-14 |
| | | Terminal sacrifice | DAY 14 |
| | 34 | Normal | DAY 0-14 |
| | | Terminal sacrifice | DAY 14 |
| | 35 | Normal | DAY 0-14 |
| | | Terminal sacrifice | DAY 14 |
| G4 (1,000) | 36 | Normal | DAY 0-14 |
| | | Terminal sacrifice | DAY 14 |
| | 37 | Normal | DAY 0-14 |
| | | Terminal sacrifice | DAY 14 |
| | 38 | Normal | DAY 0-14 |
| | | Terminal sacrifice | DAY 14 |
| | 39 | Normal | DAY 0-14 |
| | | Terminal sacrifice | DAY 14 |
| | 40 | Normal | DAY 0-14 |
| | | Terminal sacrifice | DAY 14 |

[a]The day of administration was designated as day 0.

TABLE 11

Clinical Findings in Mice
STUDY: 10-MA-337    CLINICAL SIGNS

| | | groups (mg/kg) | | | |
|---|---|---|---|---|---|
| DAYS | SIGNS | G1 (0) | G2 (10) | G3 (100) | G4 (1,000) |
| | | SEX: MALE | | | |
| 0-6 | Normal | 5/5[a] | 5/5 | 5/5 | 5/5 |
| 7 | Normal | 5/5 | 5/5 | 5/5 | 4/5 |
| | Death | 0/5 | 0/5 | 0/5 | 1/5 |
| 8-13 | Normal | 5/5 | 5/5 | 5/5 | 4/4 |
| 14 | Normal | 5/5 | 5/5 | 5/5 | 4/4 |
| | Terminal sacrifice | 5/5 | 5/5 | 5/5 | 4/4 |

TABLE 11-continued

Clinical Findings in Mice
STUDY: 10-MA-337    CLINICAL SIGNS

| | | groups (mg/kg) | | | |
|---|---|---|---|---|---|
| DAYS | SIGNS | G1 (0) | G2 (10) | G3 (100) | G4 (1,000) |
| | | SEX: FEMALE | | | |
| 0-13 | Normal | 5/5[a] | 5/5 | 5/5 | 5/5 |
| 14 | Normal | 5/5 | 5/5 | 5/5 | 5/5 |
| | Terminal sacrifice | 5/5 | 5/5 | 5/5 | 5/5 |

As can be seen in Tables 8 to 11, one female died in the 1,000 mg/kg dose group on day 7, so that the median lethal dose of the test material was calculated to be 1215.8 mg/kg (confidence interval not estimated), with no abnormal symptoms found in any of survived or dead animals.

TABLE 12

Weight Change of Mice
BODY WEIGHTS (g)
STUDY: 10-MA-337    groups (mg/kg)

| DAYS | G1 (0) | G2 (10) | G3 (100) | G4 (1,000) |
|---|---|---|---|---|
| | | SEX: MALE | | |
| DAY 0 | 33.88 ± 1.27 (5)[b] | 33.60 ± 1.11 (5) | 33.72 ± 0.75 (5) | 38.59 ± 0.76 (6) |
| DAY 1 | 38.57 ± 1.55 (5) | 33.54 ± 0.58 (5) | 33.62 ± 0.67 (5) | 33.02 ± 0.22 (5) |
| DAY 3 | 34.50 ± 0.98 (5) | 34.09 ± 1.15 (5) | 34.83 ± 0.61 (5) | 33.19 ± 1.24 (5)** |
| DAY 7 | 33.56 ± 1.38 (5) | 33.74 ± 1.43 (5) | 34.27 ± 0.68 (5) | 33.04 ± 0.75 (4) |
| DAY 14 | 35.07 ± 1.97 (5) | 36.05 ± 1.80 (5) | 35.35 ± 0.64 (5) | 35.18 ± 1.40 (4) |
| GAINS[a] | 1.69 ± 1.54 (5) | 2.45 ± 1.13 (5) | 1.63 ± 0.96 (5) | 1.80 ± 1.37 (4) |
| | | SEX: FEMALE | | |
| DAY 0 | 26.05 ± 0.88 (5) | 25.88 ± 0.84 (5) | 25.36 ± 1.01 (5) | 26.14 ± 0.64 (5) |
| DAY 1 | 26.25 ± 0.95 (5) | 26.10 ± 0.81 (5) | 26.44 ± 0.74 (5) | 25.93 ± 0.88 (5) |
| DAY 3 | 27.05 ± 1.49 (5) | 27.12 ± 0.94 (5) | 26.92 ± 0.95 (5) | 27.29 ± 1.26 (5) |
| DAY 7 | 26.73 ± 1.93 (5) | 27.57 ± 0.89 (5) | 26.70 ± 0.81 (5) | 26.96 ± 1.19 (5) |
| DAY 14 | 28.46 ± 2.15 (5) | 29.73 ± 0.88 (5) | 28.20 ± 0.75 (5) | 28.80 ± 1.42 (5) |
| GAINS[a] | 2.41 ± 1.42 (5) | 3.85 ± 0.49 (5) | 1.84 ± 0.95 (5) | 2.66 ± 1.54 (5) |

[a]Weight gains are body weight difference between day 14 and the day 0.
[b]Numbers in parenthesis represent the number of survived animals.
**A significant difference at P < 0.01 level compared with the vehicle control.

TABLE 13

Weight Change of Male Mice
STUDY: 10-MA-337    BODY WEIGHTS (g)    SEX: MALE

| groups (mg/kg) | ANIMAL ID | Day 0 | Day 1 | Day 3 | Day 7 | Day 14 | GAINS[a] |
|---|---|---|---|---|---|---|---|
| G1 (0) | 1 | 34.10 | 34.38 | 34.51 | 33.82 | 35.71 | 1.61 |
| | 2 | 31.33 | 30.99 | 33.25 | 32.57 | 32.79 | 1.46 |
| | 3 | 34.70 | 34.86 | 35.07 | 34.41 | 36.16 | 1.46 |
| | 4 | 33.31 | 34.31 | 35.77 | 35.26 | 37.41 | 4.10 |
| | 5 | 33.48 | 33.30 | 33.92 | 31.83 | 33.28 | −0.20 |
| | MEAN | 33.38 | 33.57 | 34.50 | 33.58 | 35.07 | 1.69 |
| | S.D. | 1.27 | 1.55 | 0.98 | 1.38 | 1.97 | 1.54 |
| | N | 5 | 5 | 5 | 5 | 5 | 5 |
| G2 (10) | 6 | 31.90 | 32.85 | 33.13 | 32.66 | 34.71 | 2.81 |
| | 7 | 34.42 | 34.15 | 34.99 | 34.96 | 37.07 | 2.65 |
| | 8 | 34.21 | 33.94 | 34.87 | 34.42 | 37.85 | 3.64 |
| | 9 | 33.04 | 33.01 | 32.57 | 31.79 | 33.61 | 0.57 |
| | 10 | 34.45 | 33.77 | 34.91 | 34.68 | 37.01 | 2.56 |
| | MEAN | 33.60 | 33.54 | 34.09 | 33.74 | 36.05 | 2.45 |
| | S.D. | 1.11 | 0.58 | 1.15 | 1.43 | 1.80 | 1.13 |
| | N | 5 | 5 | 5 | 5 | 5 | 5 |
| G3 (100) | 11 | 33.03 | 32.85 | 34.04 | 33.33 | 34.80 | 1.77 |
| | 12 | 33.07 | 33.14 | 34.75 | 34.37 | 36.23 | 3.16 |
| | 13 | 34.60 | 34.59 | 35.24 | 35.20 | 35.81 | 1.31 |
| | 14 | 34.53 | 33.75 | 35.60 | 34.41 | 36.00 | 0.56 |
| | 15 | 33.45 | 33.75 | 34.50 | 34.03 | 34.81 | 1.36 |

TABLE 13-continued

Weight Change of Male Mice
STUDY: 10-MA-337    BODY WEIGHTS (g)    SEX: MALE

| groups (mg/kg) | ANIMAL ID | Day 0 | Day 1 | Day 3 | Day 7 | Day 14 | GAINS[a] |
|---|---|---|---|---|---|---|---|
| | MEAN | 33.72 | 33.62 | 34.83 | 34.27 | 35.35 | 1.63 |
| | S.D. | 0.75 | 0.67 | 0.61 | 0.68 | 0.64 | 0.96 |
| | N | 5 | 5 | 5 | 5 | 5 | 5 |
| G4 (1,000) | 16 | 33.15 | 32.91 | 34.32 | 33.95 | 36.47 | 3.32 |
| | 17 | 34.03 | 32.96 | 33.16 | 33.13 | 36.30 | 2.37 |
| | 18 | 34.46 | 32.97 | 31.28 | 29.71[b] | — | — |
| | 19 | 33.80 | 33.41 | 31.39 | 32.97 | 33.86 | 0.06 |
| | 20 | 32.58 | 32.85 | 31.80 | 33.12 | 34.07 | 1.54 |
| | MEAN | 33.59 | 33.02 | 32.19 | 33.04 | 35.18 | 1.80 |
| | S.D. | 0.76 | 0.32 | 1.24 | 0.75 | 1.40 | 1.37 |
| | N | 5 | 5 | 5 | 5 | 5 | 5 |

[a]Weight gains are body weight difference between day 14 and the day 0.
[b]Body weight at the time of death.
—: Not applicable (Death).

TABLE 14

Weight Change of Female Mice
STUDY: 10-MA-337    BODY WEIGHTS (g)    SEX: FEMALE

| groups (mg/kg) | ANIMAL ID | Day 0 | Day 1 | Day 3 | Day 7 | Day 14 | GAINS[a] |
|---|---|---|---|---|---|---|---|
| G1 (0) | 21 | 27.07 | 26.87 | 28.38 | 28.36 | 30.29 | 3.22 |
| | 22 | 26.00 | 26.55 | 27.76 | 28.38 | 29.41 | 3.41 |
| | 23 | 25.22 | 25.09 | 26.59 | 36.61 | 37.48 | 2.26 |
| | 24 | 25.15 | 25.43 | 24.66 | 23.66 | 25.14 | −0.01 |
| | 25 | 36.79 | 27.31 | 27.86 | 36.65 | 39.96 | 3.17 |
| | MEAN | 26.05 | 26.25 | 27.05 | 26.73 | 28.46 | 2.41 |
| | S.D. | 0.88 | 0.95 | 1.49 | 1.93 | 2.15 | 1.42 |
| | N | 5 | 5 | 5 | 5 | 5 | 5 |
| G2 (10) | 26 | 25.22 | 25.19 | 26.16 | 26.61 | 28.79 | 3.57 |
| | 27 | 25.34 | 25.96 | 26.22 | 26.82 | 29.03 | 3.69 |
| | 28 | 26.93 | 27.20 | 28.28 | 28.44 | 30.98 | 4.05 |
| | 29 | 25.27 | 25.56 | 27.14 | 27.44 | 29.72 | 4.45 |
| | 30 | 26.66 | 26.60 | 27.79 | 28.54 | 30.13 | 3.47 |
| | MEAN | 25.88 | 26.10 | 27.12 | 27.57 | 29.73 | 3.85 |
| | S.D. | 0.84 | 0.81 | 0.94 | 0.89 | 0.88 | 0.40 |
| | N | 5 | 5 | 5 | 5 | 5 | 5 |
| G3 (100) | 31 | 24.87 | 25.35 | 25.91 | 25.53 | 27.10 | 2.23 |
| | 32 | 25.88 | 25.99 | 26.89 | 36.50 | 28.70 | 2.82 |
| | 33 | 37.05 | 26.89 | 26.05 | 37.29 | 28.28 | 1.23 |
| | 34 | 26.60 | 25.90 | 37.78 | 26.55 | 29.02 | 3.43 |
| | 35 | 37.40 | 27.06 | 27.95 | 37.63 | 37.89 | 0.49 |
| | MEAN | 26.36 | 26.44 | 26.92 | 26.70 | 28.20 | 1.84 |
| | S.D. | 1.01 | 0.74 | 0.96 | 0.81 | 0.75 | 0.95 |
| | N | 5 | 5 | 5 | 5 | 5 | 5 |
| G4 (1,000) | 36 | 26.49 | 25.41 | 25.94 | 26.57 | 26.91 | 0.42 |
| | 37 | 25.92 | 26.05 | 27.26 | 26.23 | 29.28 | 3.36 |
| | 38 | 36.42 | 26.95 | 29.27 | 28.71 | 30.82 | 4.40 |
| | 39 | 26.75 | 26.50 | 27.41 | 27.57 | 28.65 | 1.90 |
| | 40 | 25.12 | 24.72 | 26.55 | 25.72 | 28.36 | 3.24 |
| | MEAN | 26.14 | 25.93 | 27.29 | 26.96 | 28.80 | 2.66 |
| | S.D. | 0.64 | 0.88 | 1.26 | 1.19 | 1.42 | 1.54 |
| | N | 5 | 5 | 5 | 5 | 5 | 5 |

[a]Weight gains are body weight difference between day 14 and the day 0.

As is apparent from data of Tables 12 to 14, the mean weight of male mice in the 1,000 mg/kg dose group was significantly lower on day 3, compared to the vehicle control (P<0.01), but were observed to be similar to that of the control from day 7. For dead animals, a weight loss was continually observed until death.

TABLE 15

Autopsy Findings of Mice
STUDY: 10-MA-337    NECROPSY FINDINGS

| groups (mg/kg) | LOCATION | FINDINGS | FREQUENCY[a] DEAD | ALIVE |
|---|---|---|---|---|
| SEX: MALE | | | | |
| G1 (0) | | No gross findings | 0/0 | 5/5 |
| G2 (10) | | No gross findings | 0/0 | 5/5 |
| G3 (100) | | No gross findings | 0/0 | 5/5 |
| G1 (1,000) | | No gross findings | 0/1 | 4/4 |
| | Interior | Autolysis | 1/1 | 0/4 |
| SEX: FEMALE | | | | |
| G1 (0) | | No gross findings | 0/0 | 5/5 |
| G2 (10) | | No gross findings | 0/0 | 5/5 |
| G3 (100) | | No gross findings | 0/0 | 5/5 |
| G4 (1,000) | | No gross findings | 0/0 | 5/5 |

[a]Number of animals observed/Number of animals examined

TABLE 16

Autopsy Findings of Male Mice
STUDY: 10-MA-337    SEX: MALE

| groups (mg/kg) | Animal ID | FATE | LOCATION | FINDINGS |
|---|---|---|---|---|
| G1 (0) | 1 | Terminal sacrifice | | No gross findings |
| | 2 | Terminal sacrifice | | No gross findings |
| | 3 | Terminal sacrifice | | No gross findings |
| | 4 | Terminal sacrifice | | No gross findings |
| | 5 | Terminal sacrifice | | No gross findings |
| G2 (10) | 6 | Terminal sacrifice | | No gross findings |
| | 7 | Terminal sacrifice | | No gross findings |
| | 8 | Terminal sacrifice | | No gross findings |
| | 9 | Terminal sacrifice | | No gross findings |
| | 10 | Terminal sacrifice | | No gross findings |
| G3 (100) | 11 | Terminal sacrifice | | No gross findings |
| | 12 | Terminal sacrifice | | No gross findings |
| | 13 | Terminal sacrifice | | No gross findings |
| | 14 | Terminal sacrifice | | No gross findings |
| | 15 | Terminal sacrifice | | No gross findings |
| G4 (1,000) | 16 | Terminal sacrifice | | No gross findings |
| | 17 | Terminal sacrifice | | No gross findings |
| | 18 | Death | Interior | Autolysis |
| | 19 | Terminal sacrifice | | No gross findings |
| | 20 | Terminal sacrifice | | No gross findings |

TABLE 17

Autopsy Findings of Female Mice
STUDY: 10-MA-337    SEX: FEMALE

| groups (mg/kg) | Animal ID | FATE | LOCATION | FINDINGS |
|---|---|---|---|---|
| G1 (0) | 21 | Terminal sacrifice | | No gross findings |
| | 22 | Terminal sacrifice | | No gross findings |
| | 23 | Terminal sacrifice | | No gross findings |
| | 24 | Terminal sacrifice | | No gross findings |
| | 25 | Terminal sacrifice | | No gross findings |
| G2 (10) | 26 | Terminal sacrifice | | No gross findings |
| | 27 | Terminal sacrifice | | No gross findings |
| | 28 | Terminal sacrifice | | No gross findings |
| | 29 | Terminal sacrifice | | No gross findings |
| | 30 | Terminal sacrifice | | No gross findings |
| G3 (100) | 31 | Terminal sacrifice | | No gross findings |
| | 32 | Terminal sacrifice | | No gross findings |
| | 33 | Terminal sacrifice | | No gross findings |
| | 34 | Terminal sacrifice | | No gross findings |
| | 35 | Terminal sacrifice | | No gross findings |
| G4 (1,000) | 36 | Terminal sacrifice | | No gross findings |
| | 37 | Terminal sacrifice | | No gross findings |
| | 38 | Terminal sacrifice | | No gross findings |
| | 39 | Terminal sacrifice | | No gross findings |
| | 40 | Terminal sacrifice | | No gross findings |

As can be seen in Tables 15 to 17, no abnormal findings were detected in survived animals with the naked eye, and dead animals had undergone autolysis after death.

Consideration and Conclusion

The above experiments were designed to examine approximate toxicity generated upon single intravenous injection of the aptamer agent E2 to ICR lineage mice.

In the experiments, the death of one male mouse in the 1,000 mg/kg dose group, when taking the weight loss observed in the same group into consideration, was attributed to the administration of the test material. Particularly, the weight of the dead animal was reduced by 14% when it was found dead, compared to the weight on day 0. The weight loss observed in the male mice of the 1,000 mg/kg dose group was, however, considered temporary because their mean weight became similar to that of the vehicle control.

From the results obtained above, it was indicated that the single intravenous injection of the aptamer agent to ICR lineage mice caused death and temporary weight loss in the male mice of the 1,000 mg/kg dose group.

In addition, no deaths were observed from the female, estimating that the approximate lethal dose (ALD) of the test material might be over 1,000 mg/kg. The test material was calculated to have a medial lethal dose ($LD_{50}$) of 1215.8 mg/kg for males (confidence interval not established).

Autopsy examination with the naked eye gave no abnormal findings in any survived animal.

5.2. DRF Toxicity Test in ICR Mice after Repetitive Intravenous Injection with Aptamer Agent for Two Weeks The test was carried out according to Notice No. 2009-116 (issued on Aug. 24, 2009 by the Korean FDA) regarding Toxicity test criteria for drugs' and Notice No. 2009-183 (issued on Dec. 22, 2009 by the Korean FDA) regarding 'Management standards for non-clinical tests.'

Materials and Methods

The specific pathogen-free (SPF) mice HsdKoat:ICR (CD-1® Koatech), 6 weeks old, were organized as followed, and administered with the aptamer agent E2.

TABLE 18

| Group | Sex | No. of Animal | Animal No. | Volume administered (mL/kg/day) | Dose (mg/kg/day) |
|---|---|---|---|---|---|
| G1[a] | M/F | 5/5 | 1-05/26-30 | 5 | 0 |
| G2 | M/F | 5/5 | 06-10/31-35 | 5 | 5 |
| G3 | M/F | 5/5 | 11-15/36-40 | 5 | 10 |
| G4 | M/F | 5/5 | 16-20/41-45 | 5 | 20 |
| G5 | M/F | 5/5 | 21-25/46-50 | 5 | 40 |

[a]Vehicle control (1X D-PBS)

The test material was intravenously injected once a day for 14 days, and the mice were examined for mortality, general symptoms, weight change, food and water intake, and organ weight, and subjected to urinalysis, ophthalmic examination, hematological and biochemical serochemical examination, and autopsy.

Results

No dead animals were observed during the period of experiment. Also, abnormal findings were not detected from any of the administered groups. Similar weight changes were observed, whether in males or females, between the test groups and the vehicle control. All animals were found to be normal, as analyzed by ophthalmic examination. Urinalysis showed that the males in the test groups had higher levels of WBC, compared to the vehicle control, with statistical significance for the groups administered with 5, 20 and 40 mg/kg/day ($P<0.05$, $P<0.01$). Other test factors of urinalysis were similar between the males of the test groups and the vehicle control. Further, no differences in all urinalysis factors were detected between females in the test groups and the vehicle control. A serological examination showed that females in the 40 mg/kg/day dose group were significantly lowered in hematocrit (HCT) level, compared to the vehicle control ($P<0.05$), with significant differences found between males in the test group and the vehicle control. As a result of hematological and biochemical analysis, both males and females in the test groups had higher sodium ion ($Na^+$) and chloride ion ($Cl^-$) levels than the vehicle control, with statistical significances of $Na^+$ for males in the groups administered with 20 mg/kg/day or greater and females in the groups administered with 5, 20 and 40 mg/kg/day, and $Cl^-$ for males in the group administered with 40 mg/kg/day and females in the groups administered with 20 mg/kg/day or greater ($P<0.05$, $P<0.01$).

Lower levels of inorganic phosphorus (IP) and calcium ions ($Ca^{2+}$) were detected from females in the 20 mg/kg/day dose group than in the vehicle control, with significance ($P<0.01$), but no dose dependence. No significant differences in organ weight were detected in either males or females between the test groups and the vehicle control. Upon autopsy examination with the naked eye, three cases of the retention of clear fluid in the uterine was observed in males of the 5 mg/kg/day dose group, which was considered as resulting from a physiological change according to the genital cycle, and other organs were found normal. In males, no abnormal organs were found.

Consideration and Conclusion

The above experiments were designed to examine approximate toxicity generated upon repetitive intravenous injections of the aptamer agent E2 to ICR lineage mice.

The increase or increasing tendency of blood $Na^+$ and $Cl^-$ levels was detected in both males and females of the groups administered with 20 mg/kg/day or greater, and exhibited dose-dependency. Since electrolytes are always homeostatic within a narrow range, the increase was considered as being attributed to the administration of the test material. However, the test material was determined as having no toxicological significance when account was taken of the fact that the modulation was kept within a normal range, with no significant change in related items.

The decrease in blood HCT level observed in females of the 40 mg/kg/day dose group was acceptable within the normal range (JANG, Seung-Hoon, JUNG Ki-Joon: Recent Study Trend of Aptamer Development, The Korean Society For Microbiology And Biotechnology).

Urine WBC was increased in the males of the test groups, but only to a trace amount (±). Since this is often found in normal animals, with no concomitant or consequent accompaniment of a significant change in related factors, the increase was determined to be not attributed to the test material.

From the results obtained above, it was indicated that the repetitive intravenous injections of the aptamer agent at a dose of 5, 10, 20 and 40 mg/kg/day to ICR mice gave rise to an increase in blood $Na^+$ and $Cl^-$ levels in the group of 20 mg/kg/day or higher, but with no significant changes in other factors.

What is claimed is:

1. An ERBB2 aptamer, which specifically binds to ERBB2, and comprises 40 to 100 nucleotides comprising a nucleotide sequence selected from the group consisting of SEQ ID NOS: 1 to 35.

2. The ERBB2 aptamer of claim 1, wherein the ERBB2 aptamer comprises of 40 to 100 nucleotides comprising the nucleotide sequence of SEQ ID NO: 7 or SEQ ID NO: 11.

3. The ERBB2 aptamer of claim 1, wherein the ERBB2 aptamer further comprises 15 to 30 nucleotides at either or both of 5' and 3' termini of the nucleotide sequence selected from the group consisting of SEQ ID NOS: 1 to 35.

4. The ERBB2 aptamer of claim 1, wherein the ERBB2 aptamer is modified by being conjugated with at least one selected from the group consisting of PEG (polyethylene glycol), idT (inverted deoxythymidine), LNA (Locked Nucleic Acid), 2'-methoxy nucleoside, 2'-amino nucleoside, 2'F-nucleoside, an amine linker, a thiol linker, and a cholesterol, at either or both of 5' and 3' termini thereof.

5. A pharmaceutical composition, comprising the ERBB2 aptamer of claim 1 as an active ingredient.

6. The pharmaceutical composition of claim 5, wherein the pharmaceutical composition is for treatment of cancer.

7. The pharmaceutical composition of claim 6, wherein the cancer is selected from the group consisting of breast cancer, colorectal cancer, lung cancer, gallbladder cancer, pancreatic cancer, and stomach cancer.

8. The pharmaceutical composition of claim 5, wherein the pharmaceutical composition is for diagnosis of cancer.

9. A method for treating cancer, comprising administering the ERBB2 aptamer of claim 1 to a subject in need of treating cancer.

10. The method of claim 9, wherein the ERBB2 aptamer comprises 40 to 100 nucleotides comprising the nucleotide sequence of SEQ ID NO: 7 or SEQ ID NO: 11.

11. The method of claim 9, wherein the ERBB2 aptamer further comprises 15 to 30 nucleotides at either or both of 5' and 3' termini of the nucleotide sequence selected from the group consisting of SEQ ID NOS: 1 to 35.

12. The method of claim 9, wherein the ERBB2 aptamer is modified by being conjugated with at least one selected from the group consisting of PEG (polyethylene glycol), idT (inverted deoxythymidine), LNA (Locked Nucleic Acid), 2'-methoxy nucleoside, 2'-amino nucleoside, 2'F-nucleoside, an amine linker, a thiol linker, and a cholesterol, at either or both of 5' and 3' terminus thereof.

13. The method of claim 9, wherein the cancer is selected from the group consisting of breast cancer, colorectal cancer, lung cancer, gallbladder cancer, pancreatic cancer, and stomach cancer.

14. A method for cancer diagnosis, comprising:
providing a biological specimen of a subject;
reacting the biological specimen with the ERBB2 aptamer of claim 1; and
measuring a binding level of the ERBB2 aptamer in the biological specimen,
wherein when the binding level of the ERBB2 aptamer in the biological sample is higher than that in a normal specimen, the subject is determined as a cancer patient.

* * * * *

SEQUENCE LISTING

```
<160> NUMBER OF SEQ ID NOS: 42

<210> SEQ ID NO 1
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      A01_A05
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 1
angnnagagn nngccngagn gccncgnaag ggcgnaacaa                                40
```

```
<210> SEQ ID NO 2
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      A02_B05
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 2
nacngggccc gnnagccncn ggcgcnccnn cgcnngngcc                               40

<210> SEQ ID NO 3
<211> LENGTH: 36
<212> TYPE: DNA
<213> ORGANISM: Artificial Sequence
<220> FEATURE:
<223> OTHER INFORMATION: core sequence represented by Clone No. 9-ER-N-
      A03_C05
<220> FEATURE:
<221> NAME/KEY: modified_base
<222> LOCATION: (1)..(36)
<223> OTHER INFORMATION: n is NapdU [5-(N-Naphthylcarboxyamide)-2'-
      deoxyuridine]

<400> SEQUENCE: 3
nnancaacgc acngagggcg ncagcnncnn nnnagg                                  36

<210> SEQ ID NO 4
<211> LENGTH: 39
<212> TYPE: DNA
<213> ORGANISM: Artificial Sequence
<220> FEATURE:
<223> OTHER INFORMATION: core sequence represented by Clone No. 9-ER-N-
      A04_D05
<220> FEATURE:
<221> NAME/KEY: modified_base
<222> LOCATION: (1)..(39)
<223> OTHER INFORMATION: n is NapdU [5-(N-Naphthylcarboxyamide)-2'-
      deoxyuridine]

<400> SEQUENCE: 4
angnagagnn ngccngagng ccncgcaagg gcgnaacag                               39

<210> SEQ ID NO 5
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      A06_E05
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 5 nccngnccccg gnnacacaa gnnaaggcag ccgcnggana                              40

<210> SEQ ID NO 6
<211> LENGTH: 40
<212> TYPE: DNA
<213> ORGANISM: Artificial Sequence
<220> FEATURE:
<223> OTHER INFORMATION: core sequence represented by Clone No. 9-ER-N-
```

```
                                     B02_F05
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 6
gncngaacac cgagannagc ngaacgaacg gnanggacgn                              40

<210> SEQ ID NO 7
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      B03_G05
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 7
nccnggcang nncganggag gccnnngann acagcccaga                              40

<210> SEQ ID NO 8
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      B04_H05
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 8
cgcgannaga ngaacgcaca anacccgnnc ngagnaaagn                              40

<210> SEQ ID NO 9
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      B08_A06
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 9
gncngaacac cgagannagc cgaacgaacg gnanggacgn                              40

<210> SEQ ID NO 10
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      B09_B06
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]
```

<400> SEQUENCE: 10
gnnagacnga acgcacngag ggccgcagcc nancngaagg                              40

<210> SEQ ID NO 11
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      B12_C06
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 11
angnnagagn nngccngagn gccncgcaag ggcgnaacaa                              40

<210> SEQ ID NO 12
<211> LENGTH: 41
<212> TYPE: DNA
<213> ORGANISM: Artificial Sequence
<220> FEATURE:
<223> OTHER INFORMATION: core sequence represented by Clone No. 9-ER-N-
      C03_E06
<220> FEATURE:
<221> NAME/KEY: modified_base
<222> LOCATION: (1)..(41)
<223> OTHER INFORMATION: n is NapdU [5-(N-Naphthylcarboxyamide)-2'-
      deoxyuridine]

<400> SEQUENCE: 12
gncngagcan cgcgnnnagc cgaacgcncg gngaggnaga n                            41

<210> SEQ ID NO 13
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      C05_F06
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 13
ncanggcang nncganggag gccnnngann acagcccaga                              40

<210> SEQ ID NO 14
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      C06_G06
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 14
cnacacgaan caacncccn ccgcanacng aacancacaa                               40

<210> SEQ ID NO 15
<211> LENGTH: 39

```
<212> TYPE: DNA
<213> ORGANISM: Artificial Sequence
<220> FEATURE:
<223> OTHER INFORMATION: core sequence represented by Clone No. 9-ER-N-
      C08_H06
<220> FEATURE:
<221> NAME/KEY: modified_base
<222> LOCATION: (1)..(39)
<223> OTHER INFORMATION: n is NapdU [5-(N-Naphthylcarboxamide)-2'-
      deoxyuridine]

<400> SEQUENCE: 15
nnagcaaaan gccangngcg nccngncccg gnnnacagc                              39

<210> SEQ ID NO 16
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      C10_A07
<220> FEATURE:
<221> NAME/KEY: modified_base
<222> LOCATION: (1)..(40)
<223> OTHER INFORMATION: n is NapdU [5-(N-Naphthylcarboxamide)-2'-
      deoxyuridine]

<400> SEQUENCE: 16
ngangncccc aacncagcng ngaancnang cccccgccca                             40

<210> SEQ ID NO 17
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      D01_B07
<220> FEATURE:
<221> NAME/KEY: modified_base
<222> LOCATION: (1)..(40)
<223> OTHER INFORMATION: n is NapdU [5-(N-Naphthylcarboxamide)-2'-
      deoxyuridine]

<400> SEQUENCE: 17
cngagcggnn acnacaccac cgngagaccn nagnnacaaa                             40

<210> SEQ ID NO 18
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      D02_C07
<220> FEATURE:
<221> NAME/KEY: modified_base
<222> LOCATION: (1)..(40)
<223> OTHER INFORMATION: n is NapdU [5-(N-Naphthylcarboxamide)-2'-
      deoxyuridine]

<400> SEQUENCE: 18
annagangaa agcgcanncc aacaacagan aancngaggg                             40

<210> SEQ ID NO 19
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      D04_E07
<220> FEATURE:
<221> NAME/KEY: modified_base
```

-continued

<222> LOCATION: (1)..(40)
<223> OTHER INFORMATION: n is NapdU [5-(N-Naphthylcarboxyamide)-2'-
      deoxyuridine]

<400> SEQUENCE: 19
nnnggagngn cnnacggnng gagnaancga ggangganga                                40

<210> SEQ ID NO 20
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      D05_F07
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 20
ccgnnaccna ccnccncgac cgngggngcc cnnagnccca                                40

<210> SEQ ID NO 21
<211> LENGTH: 39
<212> TYPE: DNA
<213> ORGANISM: Artificial Sequence
<220> FEATURE:
<223> OTHER INFORMATION: core sequence represented by Clone No. 9-ER-N-
      D06_G07
<220> FEATURE:
<221> NAME/KEY: modified_base
<222> LOCATION: (1)..(39)
<223> OTHER INFORMATION: n is NapdU [5-(N-Naphthylcarboxyamide)-2'-
      deoxyuridine]

<400> SEQUENCE: 21
nccnggcang nncganggag gccnnngann acagccaga                                 39

<210> SEQ ID NO 22
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      D07_H07
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 22
ccgnnaccna ccnccncgac cgngggngcc nnnagnccca                                40

<210> SEQ ID NO 23
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      D09_A08
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 23
angnnagagn nngccngagn gccncgcaag ggcgnaacaa                                40

<210> SEQ ID NO 24
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      D11_B08
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 24
nccnggcang nncganggag gccnnngann acagcccagn                    40

<210> SEQ ID NO 25
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      E04_D08
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 25
annagangaa agcacanncc aacaacagan aancngaggg                    40

<210> SEQ ID NO 26
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      E11_F08
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 26
angnnagagn nngccngagn gcgncgcaag ggcgnaacag                    40

<210> SEQ ID NO 27
<211> LENGTH: 39
<212> TYPE: DNA
<213> ORGANISM: Artificial Sequence
<220> FEATURE:
<223> OTHER INFORMATION: core sequence represented by Clone No. 9-ER-N-
      E12_G08
<220> FEATURE:
<221> NAME/KEY: modified_base
<222> LOCATION: (1)..(39)
<223> OTHER INFORMATION: n is NapdU [5-(N-Naphthylcarboxyamide)-2'-
      deoxyuridine]

<400> SEQUENCE: 27
ngagaagggc ngngccnnac ncaaaannng ggancngaa                     39

<210> SEQ ID NO 28
<211> LENGTH: 40
<212> TYPE: DNA
<213> ORGANISM: Artificial Sequence
<220> FEATURE:

<223> OTHER INFORMATION: core sequence represented by Clone No. 9-ER-N-
F05_D09
<220> FEATURE:
<221> NAME/KEY: modified_base
<222> LOCATION: (1)..(40)
<223> OTHER INFORMATION: n is NapdU [5-(N-Naphthylcarboxyamide)-2'-
deoxyuridine]

<400> SEQUENCE: 28
nccnggnang nncganggag gccnnngann acagcccaga                                40

<210> SEQ ID NO 29
<211> LENGTH: 40
<212> TYPE: DNA
<213> ORGANISM: Artificial Sequence
<220> FEATURE:
<223> OTHER INFORMATION: core sequence represented by Clone No. 9-ER-N-
F08_E09
<220> FEATURE:
<221> NAME/KEY: modified_base
<222> LOCATION: (1)..(40)
<223> OTHER INFORMATION: n is NapdU [5-(N-Naphthylcarboxyamide)-2'-
deoxyuridine]

<400> SEQUENCE: 29
nagancncng annaggnaga acgcccnacn cnaacggcag                                40

<210> SEQ ID NO 30
<211> LENGTH: 40
<212> TYPE: DNA
<213> ORGANISM: Artificial Sequence
<220> FEATURE:
<223> OTHER INFORMATION: core sequence represented by Clone No. 9-ER-N-
F09_F09
<220> FEATURE:
<221> NAME/KEY: modified_base
<222> LOCATION: (1)..(40)
<223> OTHER INFORMATION: n is NapdU [5-(N-Naphthylcarboxyamide)-2'-
deoxyuridine]

<400> SEQUENCE: 30
ngagaagggc ngngccnnac ncaaaannng gggancngaa                                40

<210> SEQ ID NO 31
<211> LENGTH: 40
<212> TYPE: DNA
<213> ORGANISM: Artificial Sequence
<220> FEATURE:
<223> OTHER INFORMATION: core sequence represented by Clone No. 9-ER-N-
F11_G09
<220> FEATURE:
<221> NAME/KEY: modified_base
<222> LOCATION: (1)..(40)
<223> OTHER INFORMATION: n is NapdU [5-(N-Naphthylcarboxyamide)-2'-
deoxyuridine]

<400> SEQUENCE: 31
ngagaagggc ngngccnnac ncaaaannng gggancngaa                                40

<210> SEQ ID NO 32
<211> LENGTH: 40
<212> TYPE: DNA
<213> ORGANISM: Artificial Sequence
<220> FEATURE:
<223> OTHER INFORMATION: core sequence represented by Clone No. 9-ER-N-
G04_B10
<220> FEATURE:
<221> NAME/KEY: modified_base
<222> LOCATION: (1)..(40)
<223> OTHER INFORMATION: n is NapdU [5-(N-Naphthylcarboxyamide)-2'-
deoxyuridine]

```
<400> SEQUENCE: 32
cgnccnnggn gagnnngggn cngagcagga gcacgngagn                            40

<210> SEQ ID NO 33
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      H01_E10
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 33
annagangaa agcacanncc aacaacagan aancngaggg                            40

<210> SEQ ID NO 34
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      H03_G10
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 34
annagangaa agcacanncc aacaacagan aancngaggg                            40

<210> SEQ ID NO 35
<211> LENGTH: 40
<212> TYPE: DNA
<213> ORGANISM: Artificial Sequence
<220> FEATURE:
<223> OTHER INFORMATION: core sequence represented by Clone No. 9-ER-N-
      H09_B11
<220> FEATURE:
<221> NAME/KEY: modified_base
<222> LOCATION: (1)..(40)
<223> OTHER INFORMATION: n is NapdU [5-(N-Naphthylcarboxyamide)-2'-
      deoxyuridine]

<400> SEQUENCE: 35
angnnagagn cngccngagn gccncgcaag ggcgnaacag                            40

<210> SEQ ID NO 36
<211> LENGTH: 74
<212> TYPE: DNA
<213> ORGANISM: Artificial Sequence
<220> FEATURE:
<223> OTHER INFORMATION: antisense library
<220> FEATURE:
<221> NAME/KEY: modified_base
<222> LOCATION: (1)..(74)
<223> OTHER INFORMATION: n is any one selected from consiting of A, G,
      C, T, and NapdU

<400> SEQUENCE: 36
ggctggtggt gtggctgnnn nnnnnnnnn nnnnnnnnnn nnnnnnnnnn nnnnnnncag       60
gcagacggtc actc                                                        74
```

```
<210> SEQ ID NO 37
<211> LENGTH: 74
<212> TYPE: DNA
<213> ORGANISM: Artificial Sequence
<220> FEATURE:
<223> OTHER INFORMATION: #12 Clone(1194-1)
<220> FEATURE:
<221> NAME/KEY: modified_base
<222> LOCATION: (1)..(74)
<223> OTHER INFORMATION: n is NapdU [5-(N-Naphthylcarboxyamide)-2'-
      deoxyuridine]

<400> SEQUENCE: 37
gagtgaccgt ctgcctgang nnagagnnng ccngagngcc ncgcaagggc gnaacaacag     60
ccacaccacc agcc                                                      74

<210> SEQ ID NO 38
<211> LENGTH: 74
<212> TYPE: DNA
<213> ORGANISM: Artificial Sequence
<220> FEATURE:
<223> OTHER INFORMATION: #12 clone(1194-2)
<220> FEATURE:
<221> NAME/KEY: modified_base
<222> LOCATION: (1)..(74)
<223> OTHER INFORMATION: n is NapdU [5-(N-Naphthylcarboxyamide)-2'-
      deoxyuridine]

<400> SEQUENCE: 38
gagtgaccgt ctgcctgncc nggcangnnc ganggaggcc nnngannaca gcccagacag     60
ccacaccacc agcc                                                      74

<210> SEQ ID NO 39
<211> LENGTH: 18
<212> TYPE: DNA
<213> ORGANISM: Artificial Sequence
<220> FEATURE:
<223> OTHER INFORMATION: 5' end of ERBB2 aptamer

<400> SEQUENCE: 39
gagtgaccgt ctgcctga                                                  18

<210> SEQ ID NO 40
<211> LENGTH: 17
<212> TYPE: DNA
<213> ORGANISM: Artificial Sequence
<220> FEATURE:
<223> OTHER INFORMATION: 5' end of ERBB2 aptamer

<400> SEQUENCE: 40
ggctggtggt gtggctg                                                   17

<210> SEQ ID NO 41
<211> LENGTH: 17
<212> TYPE: DNA
<213> ORGANISM: Artificial Sequence
<220> FEATURE:
<223> OTHER INFORMATION: 3' end of ERBB2 aptamer

<400> SEQUENCE: 41
caggcagacg gtcactc                                                   17

<210> SEQ ID NO 42
<211> LENGTH: 17
<212> TYPE: DNA
<213> ORGANISM: Artificial Sequence
<220> FEATURE:
```

```
<223> OTHER INFORMATION: 3' end of ERBB2 aptamer

<400> SEQUENCE: 42
cagccacacc accagcc                                                    17
```